United States Patent [19]

Straub et al.

[11] Patent Number: 5,721,248

[45] Date of Patent: Feb. 24, 1998

[54] 4-BICYCLICALLY SUBSTITUTED DIHYDROPYRIDINES, AND THEIR USE IN MEDICAMENTS

[75] Inventors: Alexander Straub; Siegfried Goldmann, both of Wuppertal; Jürgen Stoltefuss, Haan; Martin Bechem, Wuppertal; Klaus Dembowsky; Rainer Gross, both of Wuppertal; Siegbert Hebisch, Bottrop; Joachim Hütter; Howard-Paul Rounding, both of Wuppertal, all of Germany

[73] Assignee: Bayer Aktiengesellschaft, Leverkusen, Germany

[21] Appl. No.: 644,880

[22] Filed: May 10, 1996

Related U.S. Application Data

[62] Division of Ser. No. 261,585, Jun. 17, 1994, Pat. No. 5,545,646.

[30] Foreign Application Priority Data

Jun. 24, 1993 [DE] Germany .................. 43 21 030.9

[51] Int. Cl.[6] .................. A61K 31/47; C07D 401/04
[52] U.S. Cl. .................. 514/314; 546/167
[58] Field of Search .................. 546/167; 514/314

[56] References Cited

U.S. PATENT DOCUMENTS

| | | | |
|---|---|---|---|
| 4,540,789 | 9/1985 | Goldmann et al. | 546/280.1 |
| 4,628,107 | 12/1986 | Goldmann et al. | 549/23 |
| 4,659,717 | 4/1987 | Wikel | 514/301 |
| 5,100,900 | 3/1992 | Stoltefuss et al. | 514/314 |

FOREIGN PATENT DOCUMENTS

| | | |
|---|---|---|
| 0123112 | 3/1984 | European Pat. Off. . |
| 0223744 | 10/1986 | European Pat. Off. . |
| 0450420 | 3/1991 | European Pat. Off. . |
| 0452712 | 3/1991 | European Pat. Off. . |
| 0538960 | 10/1992 | European Pat. Off. . |
| 0555657 | 1/1993 | European Pat. Off. . |
| 3601397 | 7/1987 | Germany . |
| 3714438 | 11/1988 | Germany . |
| 9117149 | 11/1991 | WIPO . |

OTHER PUBLICATIONS

CA 122:31504, Straub et al. 1995.
Chemical Abstracts, vol. 106, No. 3, Jan. 19, 1987 abstract No. 18852.
Chemical Abstracts, vol. 116, No. 14, Apr. 6, 1992, abstract No. 130100.
Chemical Abstracts, vol. 107, No. 13, Sep. 28, 1987, abstract No. 115496 & JP–A–62 045 586 Feb. 1987.
Chemical Abstracts, vol. 113, No. 5, Jul. 30, 1990, abstract No. 40468 & ES–A–2 005 543 Mar. 1989.
Journal of Medicinal Chemestry., vol. 35, Nov. 1992, pp. 4665–4675.
"A facile synthesis of benzo[b]thiopene drivatives", M. Watanabe, Jan. 1991, pp. 173–175; vol. 28, J. Heterocyclic Chem.
Synthetic Communications, vol. 23, No. 3, pp. 365–372, 1993; "Regioselective metalation of ortho–aminopicolines using the pivaloyl group as a directing group: Synthesis of Naphthyridines", S. Straub.

*Primary Examiner*—Jane Fan
*Attorney, Agent, or Firm*—Sprung Kramer Schaefer & Briscoe

[57] ABSTRACT

The invention relates to new 4-bicyclically substituted dihydropyridines of the general formula (I)

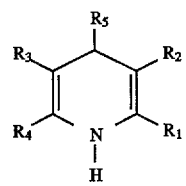

in which $R_1$ to $R_5$ have the meaning given in the description, processes for their preparation and their use in medicaments, in particular in agents for the treatment of cardiovascular diseases.

4 Claims, No Drawings

4-BICYCLICALLY SUBSTITUTED DIHYDROPYRIDINES, AND THEIR USE IN MEDICAMENTS

This application is a divisional of application Ser. No. 08/261,585, filed Jun. 17, 1994 now U.S. Pat. No. 5,545,646.

The invention relates to new 4-bicyclically substituted dihydropyridines, processes for their preparation and their use in medicaments, in particular in agents for the treatment of cardiovascular diseases.

It is already known that 1,4-dihydropyridines have vasodilatory properties and can be used as coronary agents and antihypertensives. It is furthermore known that 1,4-dihydropyridines cause inhibition of the contractility of smooth and cardiac muscles and can be employed for the treatment of coronary and vascular diseases.

4-Quinolyl-dihydropyridines having a positively inotropic action furthermore are already known from U.S. Pat. No. 5,100,900.

The present invention relates to 4-bicyclically substituted dihydropyridines of the general formula (I)

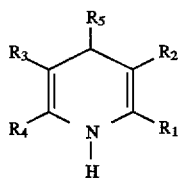

in which

R$^1$ and R$^4$ are identical or different and represent hydrogen, amino, cyano, formyl or trifluoromethyl or represent straight-chain or branched alkyl having up to 8 carbon atoms, which is optionally substituted by hydroxyl or straight-chain or branched alkoxycarbonyl having up to 6 carbon atoms or by a group of the formula —NR$^6$R$^7$, —O—CO—R$^8$, —O—(CH$_2$)$_a$—OR$^{8'}$ or —O—(CH$_2$)$_b$—NR$^9$R$^{10}$, wherein R$^6$, R$^7$, R$^9$ and R$^{10}$ are identical or different and denote hydrogen, phenyl or straight-chain or branched alkyl having up to 6 carbon atoms, R$^8$ and R$^{8'}$ are identical or different and denote straight-chain or branched alkyl having up to 6 carbon atoms, and a and b are identical or different and denote the number 2, 3, 4 or 5, R$^2$ represents cyano or represents a group of the formula —CO—NR$^{11}$R$^{12}$ or —CO—A—R$^{13}$, wherein R$^{11}$ and R$^{12}$ are identical or different and denote hydrogen or a straight-chain, branched or cyclic, saturated or unsaturated hydrocarbon radical having up to 8 carbon atoms, which is optionally substituted by halogen, hydroxyl or cyano or by aryl, aryloxy or arylthio having in each case 6 to 10 carbon atoms or by a 5- to 7-membered, saturated or unsaturated heterocyclic radical having up to 3 hetero atoms from the series comprising S, N and O, it being possible for the cyclic radicals in turn to be substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denote aryl having 6 to 10 carbon atoms or a 5- to 7-membered, saturated or unsaturated heterocyclic radical having up to 3 hereto atoms from the series comprising S, N and O, which are optionally substituted up to twice in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or R$^{11}$ and R$^{12}$, together and including the nitrogen atom, form a 3- to 8-membered, saturated or unsaturated heterocyclic radical, which can optionally be interrupted by an oxygen atom or by a radical of the formula S(O)$_d$, —CO— or —NR$^{15}$—, wherein d denotes the number 0, 1 or 2, R$^{15}$ denotes hydrogen or aryl having 6 to 10 carbon atoms, which is optionally substituted up to twice in an identical or different manner by halogen or cyano or by straight-chain or branched alkyl, alkoxy, alkylthio, alkoxycarbonyl having in each case up to 8 carbon atoms or halogenoalkyl, halogenoalkoxy or halogenoalkylthio having in each case up to 4 carbon atoms, or denotes a cyclic, straight-chain or branched, saturated or unsaturated hydrocarbon radical having up to 8 carbon atoms, which is optionally substituted by hydroxyl or halogen or by aryl having 6 to 10 carbon atoms or a 5- to 7-membered, saturated or unsaturated heterocyclic radical having up to 3 hetero atoms from the series comprising S, N end O, it being possible for the cyclic radicals in turn to be substituted up to twice in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and the heterocyclic radical is optionally substituted by straight-chain or branched alkoxy or alkylthio having in each case up to 4 carbon atoms, halogen, aryl having 6 to 10 carbon atoms or a 5- to 7-membered, saturated or unsaturated heterocyclic radical having up to 3 hetero atoms from the series comprising S, N and O or by straight-chain or branched alkyl having up to 4 carbon atoms, which in turn can be substituted by aryl having 6 to 10 carbon atoms, A denotes a direct bond or an oxygen atom, R$^{13}$ denotes hydrogen or aryl having 6 to 10 carbon atoms or a 5- to 7-membered, saturated or unsaturated heterocyclic radical having up to 3 hetero atoms from the series comprising S, N and O, the cyclic radicals optionally being substituted up to 3 times in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denotes a cyclic, straight-chain or branched, saturated or unsaturated hydrocarbon radical having up to 10 carbon atoms, which is optionally interrupted up to 3 times in an identical or different manner by oxygen or by —CO—, —CO—NH—, —O—CO—, —CO—O—, —NH—CO—, —SO$_2$—NH—, —NH—SO$_2$—, —S(O)$_e$— or —NR$^{16}$—, wherein e has the abovementioned meaning of d and is identical to or different from this, R$^{16}$ has the abovementioned meaning of R$^{15}$ and is identical to or different from this, or the hydrocarbon radical is optionally interrupted up to 3 times in an identical or different by arylidene having 6 to 10 carbon atoms or heterocyclic radicals of the formulae

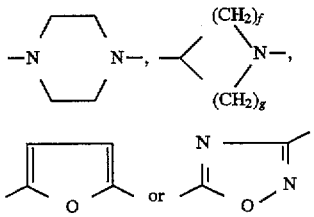

wherein f and g are identical or different and denote the number 1 or 2, and wherein arylidene can be substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and the hydrocarbon radical is optionally substituted up to 3 times in an identical or different manner by cycloalkyl having 3 to 8 carbon atoms, halogen, nitro, cyano, hydroxyl, —O—$NO_2$ or straight-chain or branched alkylthio, alkoxy or acyloxy having in each case up to 8 carbon atoms or by aryl, aryloxy or arylthio having in each case 6 to 10 carbon atoms or by a 5- to 7-membered, saturated or unsaturated heterocyclic radical having up to 3 hetero atoms from the series comprising S, N and O, it being possible for the cyclic radicals in turn to be substituted up to 3 times in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or the hydrocarbon radical is optionally substituted by a group of the formula —$CO_2$—$R^{17}$, —$CONR^{18}R^{19}$, —$NR^{20}R^{21}$ or —$NR^{22}$—$CO_2R^{23}$, wherein $R^{17}$ has the abovementioned meaning of $R^{15}$ and is identical to or different from this and $R^{18}$, $R^{19}$, $R^{20}$, $R^{21}$, $R^{22}$ and $R^{23}$ have the abovementioned meaning of $R^{11}$ and $R^{12}$ and are identical to or different from these, $R^3$ represents cyano, nitro, formyl or straight-chain or branched alkoxycarbonyl having up to 6 carbon atoms, which is optionally substituted by straight-chain or branched alkoxy having up to 6 carbon atoms, or represents a group of the formula —CO—NH—G, wherein G denotes cycloalkyl having 3 to 6 carbon atoms, or $R^3$ and $R^4$ together form a radical of the formula

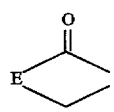

wherein

E denotes an oxygen or sulphur atom or the —$(CH_2)_n$— group, wherein n denotes the number 1 or 2, $R^5$ represents a radical of the formula

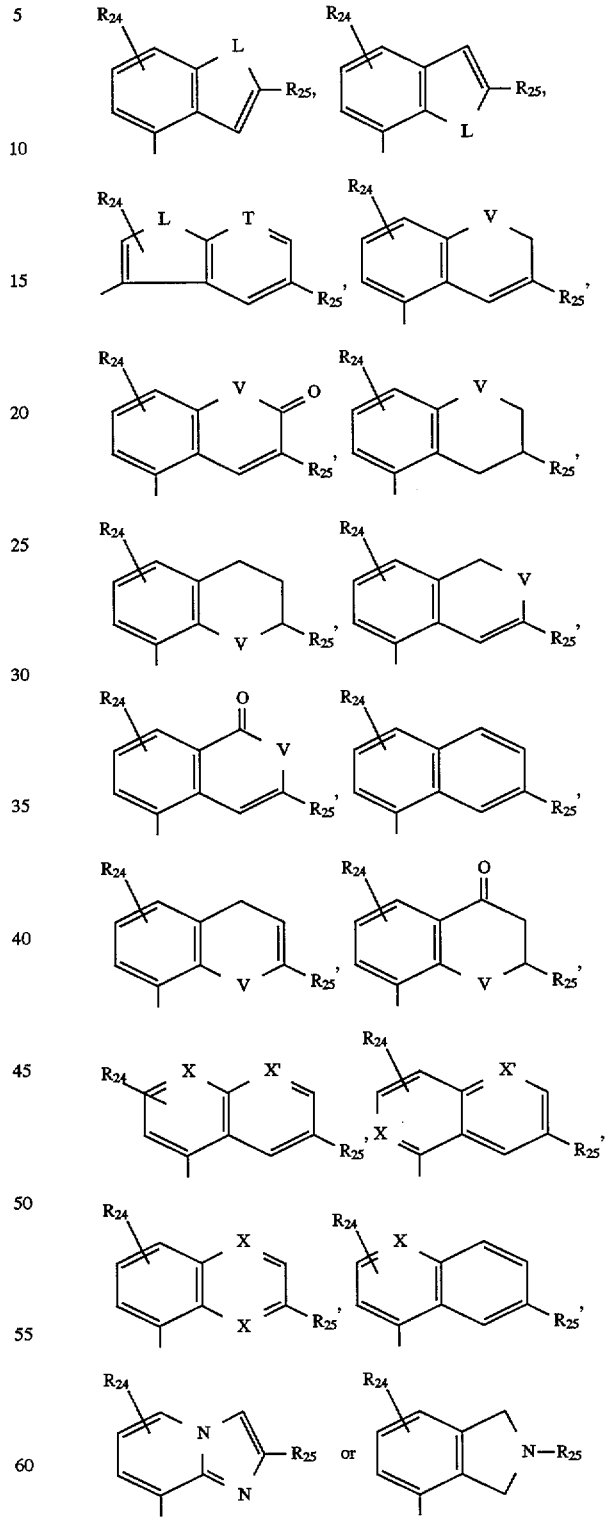

wherein $R^{24}$ denotes hydrogen, halogen or straight-chain or branched alkyl or alkoxy having in each case up to 8 carbon atoms, $R^{25}$ denotes aryl having 6 to 10 carbon atoms, which is optionally substituted up to 3 times in an identical or different manner by halogen, nitro, cyano, trifluoromethyl, trifluoromethoxy or trifluoromethylthio, or by straight-chain or branched alkyl having up to 8 carbon atoms, which can in turn be substituted by aryl having 6 to 10 carbon atoms, or is substituted by straight-chain or branched alkoxy or alkoxycarbonyl having in each case up to 8 carbon atoms, carboxyl or amino or by a group of the formula $-NR^{26}R^{27}$, wherein $R^{26}$ and $R^{27}$ are identical or different and denote hydrogen, straight-chain or branched alkyl having up to 8 carbon atoms, phenyl or benzyl, or $R^{25}$ denotes a cyclic, straight-chain or branched, saturated or unsaturated hydrocarbon radical having up to 12 carbon atoms, which is optionally interrupted up to twice in an identical or different manner by oxygen or sulphur, and which is optionally substituted up to 3 times in an identical or different manner by cycloalkyl having 3 to 8 carbon atoms, straight-chain or branched acyloxy having up to 4 carbon atoms, halogen, nitro, cyano or hydroxyl or by aryl, aryloxy or arylthio having in each case 6 to 10 carbon atoms or by a 5- to 7-membered, saturated or unsaturated optionally fused heterocyclic radical having up to 5 hetero atoms from the series comprising S, N and O, it being possible for the cyclic radicals in turn to be substituted up to 3 times in an identical or different manner by halogen, cyano, nitro or hydroxyl or by straight-chain or branched alkyl or alkoxy having in each case up to 4 carbon atoms, trifluoromethyl, trifluoromethoxy or trifluoromethylthio or by a group of the formula $-NR^{28}R^{29}$, wherein $R^{28}$ and $R^{29}$ have the abovementioned meaning of $R^{11}$ and $R^{12}$ and are identical to or different from these, or the hydrocarbon radical is optionally substituted by a group of the formula $-CO_2-R^{30}$, $-CONR^{31}R^{32}$, $-NR^{33}R^{34}$, $-NR^{35}-CO_2R^{36}$ or $-NR^{37}-SO_2R^{38}$, wherein $R^{30}$ has the abovementioned meaning of $R^{15}$ and is identical to or different from this and $R^{31}$, $R^{32}$, $R^{33}$, $R^{34}$, $R^{35}$, $R^{36}$, $R^{37}$ and $R^{38}$ have the abovementioned meaning of $R^{11}$ and $R^{12}$ and are identical to or different from these, or $R^{25}$ denotes a 5- to 7-membered, saturated or unsaturated heterocyclic radical having up to 4 hetero atoms from the series comprising S, N and O, which is optionally substituted up to 3 times in an identical or different manner by halogen, amino, cyano or nitro or by straight-chain or branched alkyl, alkoxy, alkylthio, alkoxycarbonyl, halogenoalkyl, halogenoalkoxy or halogenoalkylthio having in each case up to 4 carbon atoms or by $C_1-C_4$-mono- or -dialkylamino, or $R^{25}$ denotes a group of the formula $D-R^{39}$, wherein D denotes the CO— or $-S(O)_h-$ group or an oxygen atom, wherein h denotes the number 0, 1 or 2, and $R^{39}$ denotes aryl having 6 to 10 carbon atoms or a 5- to 7-membered, saturated or unsaturated heterocyclic radical having up to 3 hetero atoms from the series comprising S, N and O, which is optionally substituted up to 3 times in an identical or different manner by halogen, amino, cyano or nitro or by straight-chain or branched alkyl, alkoxy, alkylthio, alkoxycarbonyl, halogenoalkyl, halogenoalkoxy or halogenoalkylthio having in each case up to 4 carbon atoms or by $C_1-C_4$-mono- or -dialkylamino, or $R^{39}$ denotes hydrogen or a cyclic, straight-chain or branched, saturated or unsaturated hydrocarbon radical having up to 8 carbon atoms, which is optionally interrupted by oxygen or sulphur, and which is optionally substituted by halogen, aryl, aryloxy or arylthio having in each case 6 to 10 carbon atoms or by a 5- to 7-membered, saturated or unsaturated heterocyclic radical having up to 3 hetero atoms from the series comprising S, N and O, it being possible for the cyclic radicals in turn to be substituted by halogen, trifluoromethyl, methyl, methoxy, nitro or methylthio, or is substituted by a group of the formula $-NR^{40}R^{41}$ wherein $R^{40}$ and $R^{41}$ have the abovementioned meaning of $R^{11}$ and $R^{12}$ and are identical to or different from these, L denotes a sulphur or oxygen atom or the —NH— group, T denotes a nitrogen atom or the N→O group, V denotes a sulphur or oxygen atom and X end X' are identical or different and denote a nitrogen atom or the N→O group, and salts thereof.

Physiologically acceptable salts can be salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention exist in stereoisomeric forms which are either mirror images of one another (enantiomers) or are not (diastereomers). The invention relates both to the antipodes and to the racemic forms as well as the diastereomer mixtures. The racemic forms, like the diastereomers, can be separated into the stereoisomerically uniform constituents in a known manner.

Preferred compounds of the general formula (I) are those in which $R^1$ and $R^4$ are identical or different and represent hydrogen, amino, cyano, formyl or trifluoromethyl, or represent straight-chain or branched alkyl having up to 4 carbon atoms, which is optionally substituted by hydroxyl or straight-chain or branched alkoxycarbonyl having up to 4 carbon atoms or by a group of the formula $-NR^6R^7$, $-O-CO-R^8$, $-O-(CH_2)_a-OR^{8'}$ or $-O-(CH_2)_b-NR^9R^{10}$, wherein $R^6$, $R^7$, $R^9$ and $R^{10}$ are identical or different and denote hydrogen or straight-chain or branched alkyl having up to 4 carbon atoms, $R^8$ and $R^{8'}$ are identical or different and denote straight-chain or branched alkyl having up to 4 carbon atoms, and a and b are identical or different and denote the number 2, 3, 4 or 5, $R^2$ represents cyano, or represents a group of the formula —CO—NR$^{11}$R$^{12}$ or —CO—A—R$^{13}$, wherein $R^{11}$ and $R^{12}$ are identical or different and denote hydrogen or a straight-chain, branched or cyclic, saturated or unsaturated hydrocarbon radical having up to 6 carbon atoms, which is optionally substituted by fluorine, chlorine, hydroxyl, phenyl or pyridyl, it being possible for the cyclic radicals in turn to be substituted by fluorine or chlorine or by alkyl, alkoxy, alkylthio or alkoxycarbonyl having in each case up to 2 carbon atoms, trifluoromethyl or trifluoromethoxy, or denote phenyl or pyridyl, which are optionally substituted by fluorine or chlorine or by alkyl, alkoxy, alkylthio or alkoxycarbonyl having in each case up to 2 carbon atoms, trifluoromethyl or trifluoromethoxy, or $R^{11}$ and $R^{12}$, together and including the nitrogen atom, form a 3- to 8-membered, saturated or unsaturated heterocyclic radical, which can optionally be interrupted by an oxygen atom or by a radical of the formula S(O)$_d$, —CO— or —NR$^{15}$—, wherein d denotes the number 0, 1 or 2, $R^{15}$ denotes hydrogen or phenyl, which is optionally substituted by fluorine, chlorine, methyl, ethyl, methoxy, ethoxy, trifluoromethyl or trifluoromethoxy, or denotes a cyclic, straight-chain or branched, saturated or unsaturated hydrocarbon radical having up to 4 carbon atoms, which is optionally substituted by fluorine, chlorine or phenyl or by a 5- to 7-membered, saturated or unsaturated heterocyclic radical having up to 3 hetero atoms from the series comprising S, N end O, it being possible for the cyclic radicals in turn to be substituted by fluorine, chlorine, methyl, methoxy, methylthio, trifluoromethyl or trifluoromethoxy, A denotes a direct bond or an oxygen atom, $R^{13}$ denotes hydrogen, phenyl or pyridyl, which are optionally substituted by fluorine, chlorine, methyl, methoxy, methylthio, trifluoromethyl or trifluoromethoxy, or denotes a cyclic, straight-chain or branched, saturated or unsaturated hydrocarbon radical having up to 8 carbon atoms, which is optionally interrupted up to twice in an identical or different manner by oxygen or by —CO—, —CO—NH—, —O—CO—, —CO—O—, —NH—CO—, —SO$_2$—NH—, —NH—SO$_2$—, —S(O)$_e$— or —NR$^{16}$—, wherein e has the abovementioned meaning of d and is identical to or different from this, $R^{16}$ has the abovementioned meaning of $R^{15}$ and is identical to or different from this, or the hydrocarbon radical is optionally interrupted up to twice in an identical or different manner by arylidene having 6 to 10 carbon atoms or heterocyclic radicals of the formulae

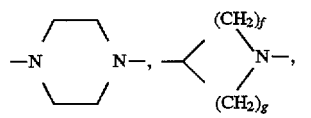

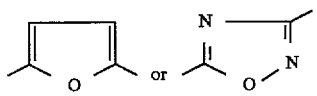

wherein f and g are identical or different and denote the number 1 or 2, and the hydrocarbon radical is optionally substituted up to twice in an identical or different manner by cyclopropyl, cyclobutyl, cyclopentyl, cyclohexyl, fluorine, chlorine, nitro, cyano, hydroxyl, —O—NO$_2$— or straight-chain or branched alkylthio, alkoxy or acyloxy having in each case up to 4 carbon atoms or by phenyl, phenoxy, phenylthio or pyridyl, it being possible for the cyclic radicals in turn to be substituted by fluorine, chlorine, cyano, methyl, methoxy, methylthio, trifluoromethyl or trifluoromethoxy, or the hydrocarbon radical is optionally substituted by a group of the formula —CO$_2$13 R$^{17}$, —CONR$^{18}$R$^{19}$, —NR$^{20}$R$^{21}$ or —NR$^{22}$—CO$_2$R$^{23}$, wherein $R^{17}$ has the abovementioned meaning of $R^{15}$ and is identical to or different from this and $R^{18}$, $R^{19}$, $R^{20}$, $R^{21}$, $R^{22}$ and $R^{23}$ have the abovementioned meaning of $R^{11}$ and $R^{12}$ and are identical to or different from these, $R^3$ represents cyano, nitro, formyl or straight-chain or branched alkoxycarbonyl having up to 4 carbon atoms, which is optionally substituted by straight-chain or branched alkoxy having up to 4 carbon atoms, or represents a group of the formula —CO—NH—G, wherein G denotes cyclopropyl, cyclopentyl or cyclohexyl, or $R^3$ and $R^4$ together form a radical of the formula

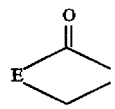

wherein

E denotes an oxygen or sulphur atom or the —(CH$_2$)$_n$— group, wherein n denotes the number 1 or 2, $R^3$ represents a radical of the formula

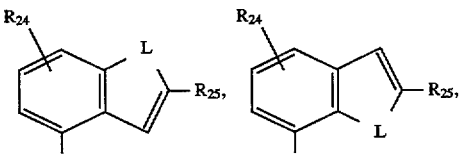

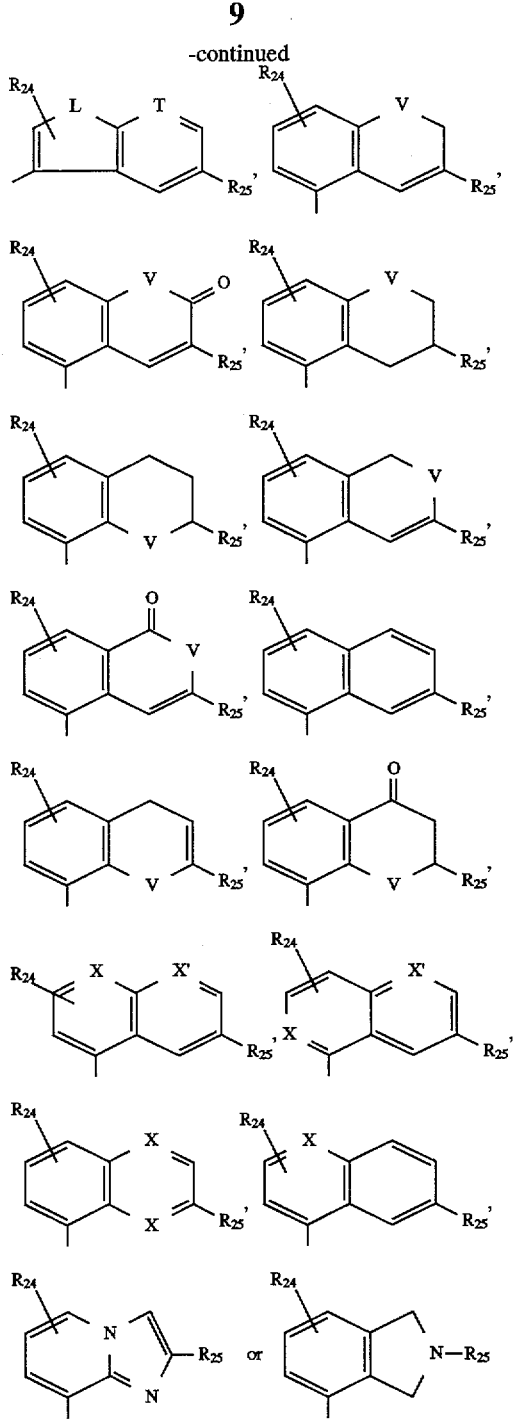

R²⁴ denotes hydrogen, fluorine or chlorine,

R²⁵ denotes phenyl, which is optionally substituted up to twice in an identical or different manner by halogen, nitro, cyano or trifluoromethyl or by straight-chain or branched alkyl or alkoxy having in each case up to 4 carbon atoms or by a group of the formula —NR²⁶R²⁷, wherein and R²⁶ and R²⁷ are identical or different and denote hydrogen, straight-chain or branched alkyl having up to 6 carbon atoms, phenyl or benzyl, or R²⁵ denotes a cyclic, straight-chain or branched, saturated or unsaturated hydrocarbon radical having up to 10 carbon atoms, which is optionally interrupted by oxygen or sulphur, and which is optionally substituted up to twice in an identical or different manner by cyclopropyl, cyclobutyl, cyclopentyl, cyclohexyl, fluorine, chlorine, bromine, acyloxy having up to 4 carbon atoms, cyano or hydroxyl or by phenyl, phenyloxy or phenylthio or by a 5- to 7-membered, saturated or unsaturated heterocyclic radical having up to 3 hetero atoms from the series comprising S, N and O, it being possible for the phenyl cyclic radicals and the heterocyclic radicals in turn to be substituted up to twice in an identical or different manner by fluorine, chlorine, bromine, hydroxyl, methyl, ethyl, methoxy, ethoxy, trifluoromethyl, trifluoromethoxy or trifluoromethylthio or by a group of the formula —NR²⁸R²⁹, wherein R²⁸ and R²⁹ have the abovementioned meaning of R¹¹ and R¹² and are identical to or different from these, and the hydrocarbon radical is optionally substituted by a group of the formula —CO₂—R³⁰, —CONR³¹R³², —NR³³R³⁴, —NR³⁵—CO₂R³⁶ or —NR³⁷—SO₂R³⁸, wherein R³⁰ has the abovementioned meaning of R¹⁵ and is identical to or different from this and R³¹, R³², R³³, R³⁴, R³⁵, R³⁶, R³⁷ and R³⁸ have the abovementioned meaning of R¹¹ and R¹² and are identical to or different from these, or R²⁵ denotes a 5- to 7-membered, saturated or unsaturated heterocyclic radical having up to 4 hetero atoms from the series comprising S, N and O, which is optionally substituted up to twice in an identical or different manner by fluorine, chlorine, bromine, cyano or nitro or by alkyl, alkoxy, alkylthio, alkoxycarbonyl, halogenoalkyl, halogenoalkoxy or halogenoalkylthio having in each case up to 2 carbon atoms or amino or by C₁–C₄-mono- or -dialkylamino, or R²⁵ denotes a group of the formula D—R³⁹, wherein D denotes the CO— or —S(O)ₕ— group or an oxygen atom, wherein h denotes the number 0, 1 or 2, and R³⁹ denotes phenyl or a 5- to 7-membered, saturated or unsaturated heterocyclic radical having up to 3 hetero atoms from the series comprising S, N and O, which is optionally substituted up to twice in an identical or different manner by fluorine, chlorine, bromine, cyano or nitro or by straight-chain or branched alkyl, alkoxy, alkylthio, alkoxycarbonyl, halogenoalkyl, halogenoalkoxy or halogenoalkylthio having in each case up to 4 carbon atoms or amino or by C₁–C₄-mono- or -dialkylamino, or R³⁹ denotes hydrogen or a cyclic, straight-chain or branched, saturated or unsaturated hydrocarbon radical having up to 8 carbon atoms, which is optionally interrupted by oxygen or sulphur, and which can optionally be substituted by fluorine, chlorine, phenyl, phenoxy or phenylthio, or is substituted by a group of the formula —NR⁴⁰R⁴¹ wherein

R⁴⁰ and R⁴¹ have the abovementioned meaning of R¹¹ and R¹² and are identical to or different from these, L denotes a sulphur or oxygen atom or the —NR— group, T denotes a nitrogen atom or the N→O group, V denotes a sulphur or oxygen atom and X and X' are identical or different and denote a nitrogen atom or the N→O group and salts thereof.

Particularly preferred compounds of the general formula (I) are those in which

R¹ and R⁴ are identical or different and represent hydrogen, amino or straight-chin or branched alkyl having up to 3 carbon atoms, which is optionally substituted by methoxycarbonyl or by the group of the formula —O—CO—CH₃, represents cyano, or represents a group of the formula —CO—NR¹¹R¹² or —CO—A—R¹³, wherein R¹¹ and R¹² are identical or different and denote hydrogen or a straight-chain, branched or cyclic, saturated or unsaturated hydrocarbon radical having up to 6 carbon atoms, or denote phenyl, which is optionally substituted by fluorine, chlorine, methyl or methoxy, A denotes a direct bond or an oxygen atom, R¹³ denotes hydrogen or a cyclic, straight-chain or branched, saturated or unsaturated hydrocarbon radical having up to 8 carbon atoms, which is optionally interrupted by oxygen or sulphur or by —CO—NH—, —O—CO—, —CO—O—, —NH—CO—, —SO₂—NH—, —NH—SO₂— or —NR¹⁶, wherein R¹⁶ denotes hydrogen or straight-chain or branched alkyl having up to 4 carbon atoms, or the hydrocarbon radical is interrupted by heterocyclic radicals of the formulae

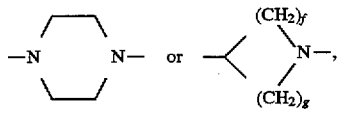

wherein f and g are identical or different and denote the number 1 or 2, and the hydrocarbon radical is optionally substituted by cyclopropyl, cyclobutyl, cyclopentyl, cyclohexyl, fluorine, chlorine, nitro, cyano or hydroxyl or by phenyl, phenoxy, phenylthio or pyridyl, which in turn can be substituted by fluorine, chlorine, methyl, methoxy, methylthio, trifluoromethyl or trifluoromethoxy, or the hydrocarbon radical is optionally substituted by a group of the formula —CO₂R¹⁷, —CONR¹⁸R¹⁹, —NR²⁰R²¹ or —NR²²—CO₂R²³, wherein R²⁰ and R²¹ are identical or different and denote hydrogen or a straight-chain, branched or cyclic, saturated or unsaturated hydrocarbon radical having up to 6 carbon atoms, which is optionally substituted by fluorine, chlorine, pyridyl or phenyl, which in turn can be substituted by fluorine, chlorine, methyl or methoxy, or denote phenyl, which is optionally substituted by fluoride, chlorine, methyl or methoxy, or R²⁰ denote phenyl, which is optionally substituted by fluorine, chlorine, methyl or methoxy, or R²⁰ and R²¹, together and including the nitrogen atom, form a 5- to 6-membered, saturated or unsaturated heterocyclic radical, which can optionally contain up to 2 further hetero atoms from the series comprising S, N and O and is optionally substituted by straight-chain or branched alkyl having up to 4 carbon atoms, benzyl or phenyl, R¹⁷, R¹⁸, R¹⁹, R²² and R²³ are identical or different and denote hydrogen or straight-chain or branched alkyl having up to 6 carbon atoms, which is optionally substituted by phenyl, or denote phenyl, which is optionally substituted by fluorine, chlorine or bromine, R³ represents cyano, nitro, formyl or straight-chain or branched alkoxycarbonyl having up to 4 carbon atoms, which is optionally substituted by straight-chain or branched alkoxy having up to 4 carbon atoms, or represents a group of the formula —CO—NH—G, wherein G denotes cyclopropyl or cyclopentyl, or R³ and R⁴ together form a radical of the formula

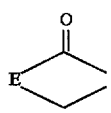

wherein

E denotes an oxygen or sulphur atom or the —(CH₂)ₙ— group, wherein n denotes the number 1 or 2, R⁵ represents a radical of the formula

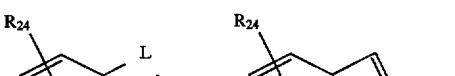

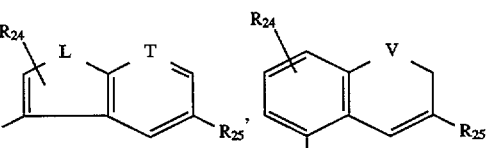

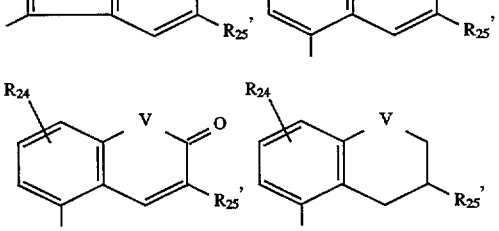

wherein

R²⁴ denotes hydrogen, fluorine or chlorine,

R²⁵ denotes phenyl, which is optionally substituted up to twice in an identical or different manner by fluorine, chlorine, nitro, trifluoromethyl, methyl, ethyl, methoxy or ethoxy or by a group of the formula —NR₂₆R²⁷,
wherein R²⁶ and R²⁷ are identical or different and denote hydrogen or straight-chain or branched alkyl having up to 4 carbon atoms, phenyl or benzyl, or R²⁵ denotes a cyclic, straight-chain or branched, saturated or unsaturated hydrocarbon radical having up to 8 carbon atoms, which is optionally interrupted by oxygen or sulphur, and which is optionally substituted by cyclopropyl, cyclobutyl, cyclopentyl, cyclohexyl, fluorine, chlorine, nitro, cyano, hydroxyl or by phenyl, phenyloxy or phenylthio or by a 5- to 7-membered, saturated or unsaturated heterocyclic radical having up to 2 hetero atoms from the series comprising S, N and O, it being possible for the phenyl cyclic radicals and the heterocyclic radicals in turn to be substituted up to twice in an identical or different manner by fluorine, chlorine, methyl, methoxy, trifluoromethyl or trifluoromethoxy or by a group of the formula —NR²⁸R²⁹,
wherein R²⁸ and R²⁹ have the abovementioned meaning of R¹¹ and R¹² and are identical to or different from these, or the hydrocarbon radical is optionally substituted by a group of the formula —CO₂R³⁰, —CONR³¹R³², —NR³³R³⁴, —NR³⁵—CO₂R³⁶ or —NR³⁷—SO₂R³⁸,
wherein R³⁰ denotes alkyl having 1–4 C atoms or phenyl,
and R³¹, R³², R³³, R³⁴, R³⁵, R³⁶, R³⁷ and R³⁸ have the abovementioned meaning of R¹¹ end R¹² and are identical to or different from these, or R²⁵ denotes a 5- to 6-membered, saturated or unsaturated heterocyclic radical having up to 2 hetero atoms from the series comprising S, N end O, which is optionally substituted by fluorine, chlorine, methyl, methoxy, methylthio or trifluoromethyl, or R²⁵ denotes a group of the formula D—R³⁹,
wherein D denotes the —S(O)ₕ group or an oxygen atom,
wherein h denotes the number 0, 1 or 2,
and R³⁹ denotes phenyl, which is optionally substituted by fluorine, chlorine, bromine, methyl, methoxy, methylthio, trifluoromethyl or amino or by $C_1$–$C_2$-mono- or -dialkylamino, or R³⁹ denotes hydrogen or a cyclic, straight-chain or branched, saturated or unsaturated hydrocarbon radical having up to 6 carbon atoms, which is optionally interrupted by oxygen or sulphur, and which is optionally substituted by fluorine, chlorine or phenyl, or is substituted by a group of the formula —NR⁴⁰R⁴¹
wherein R⁴⁰ and R⁴¹ have the abovementioned meaning of R¹¹ and R¹² and are identical to or different from these, L denotes a sulphur or oxygen atom or the —NH— group, T denotes a nitrogen atom or the N→O group, V denotes a sulphur or oxygen atom and X and X' are identical or different and denote a nitrogen atom or the N→O group and salts thereof.

Processes have furthermore been found for the preparation of the compounds of the general formula (I) according to the invention, characterized in that in the case where R³ represents cyano, nitro or formyl,

[A] compounds of the general formula (II)

$$\begin{array}{c} R^5 \\ | \\ CHO \end{array} \quad (II)$$

in which

R⁵ has the abovementioned meaning,
are first reacted with acyl compounds of the general formula (III)

$$R^3—CO—CH_2—R^4 \quad (III)$$

in which

R³ and R⁴ have the abovementioned meaning,
if appropriate with isolation of the ylidene compounds of the general formula (IV)

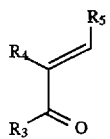 (IV)

in which

R$^3$, R$^4$ and R$^5$ have the abovementioned meaning,
and the products are then reacted with compounds of the formula (V)

 (V)

in which

R$^1$ and R$^2$ have the abovementioned meaning,
and a reactive ammonium compound, for example ammonium acetate, or directly with enamino compounds of the general formula (VI)

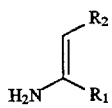 (VI)

in which

R$^1$ and R$^2$ have the abovementioned meaning, in inert solvents, or

[B] compounds of the general formula (II) are first reacted with compounds of the general formula (V), if appropriate with isolation of the ylidene compounds of the general formula (VII)

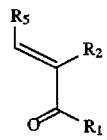 (VII)

in which

R$^1$, R$^2$ and R$^5$ have the abovementioned meaning,
and the products are then reacted either with compounds of the general formula (III) in the presence of ammonium compounds or directly with compounds of the general formula (VIII)

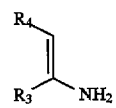 (VIII)

in which

R$^3$ and R$^4$ have the abovementioned meaning, or

[C] in the case where R$^3$ and R$^4$ together form a radical of the formula

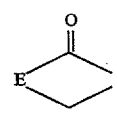

wherein

E' represents an oxygen or sulphur atom, compounds of the general formula (IX)

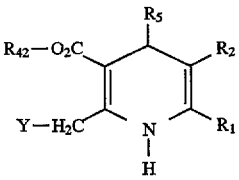 (IX)

in which

R$^1$, R$^2$ and R$^5$ have the abovementioned meaning,

R$^{42}$ represents C$_1$–C$_4$-alkyl and

Y represents C$_1$–C$_4$-acyloxy or acylthio, are first prepared by the methods described under [A] and [B], and a basic or acid cyclization is then carried out by known methods, or

[D] in that, in the case where E represents the —(CH$_2$)$_n$— group, compounds of the general formula (II) are first reacted with acyl compounds of the general formula (X)

 Z—CO—CH$_2$—R$^2$ (X)

in which

R$^2$ has the abovementioned meaning and

Z has the abovementioned meaning of R$^1$, and in the case of the hydroxyl and/or amino functions, these are present in protected form if appropriate, if appropriate with isolation of the ylidene compounds of the general formula (XI)

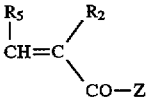 (XI)

in which

R$^2$, R$^5$ and Z have the abovementioned meaning, and the products are then reacted with the compound of the formula (XII)

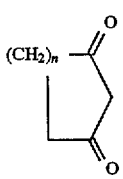 (XII)

in which n denotes the number 1 or 2, and a reactive ammonium compound, for example ammonium acetate, if appropriate with isolation of the intermediate products of the general formula (XIII)

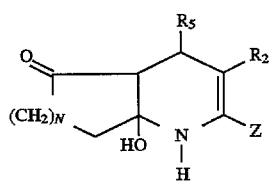 (XIII)

in which

R², R⁵, n and Z have the abovementioned meaning,
in inert solvents,
and, in a last step, water is then separated off, if appropriate in the presence of an auxiliary,
or

[E] compounds of the general formula (II) are reacted with compounds of the general formula (VIIIa) and (XIV)

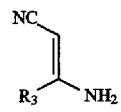
(VIIIa)

and

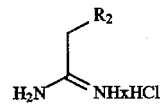
(XIV)

in which

R² and R³ have the abovementioned meaning,
in one of the abovementioned solvents.

The processes according to the invention can be illustrated by way of example by the following equations:

[A]
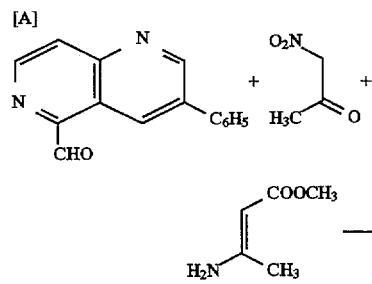

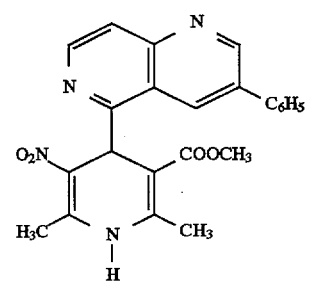

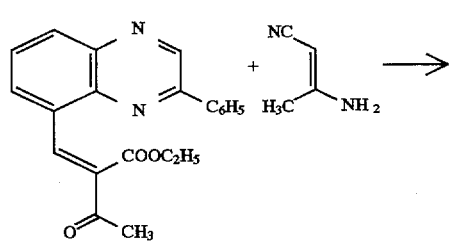

[B]
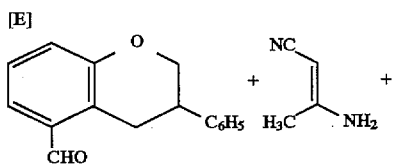

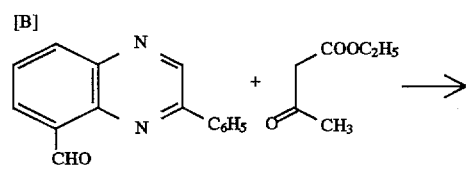

[C]
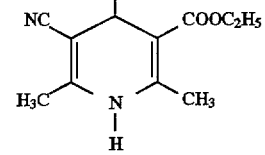

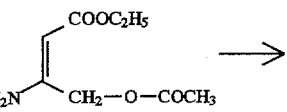

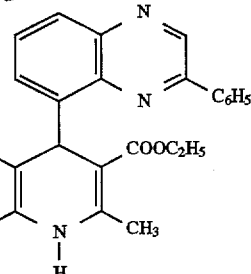

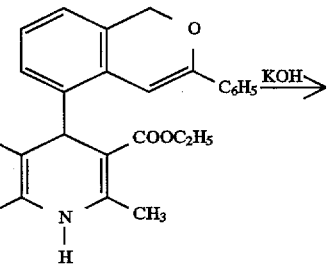

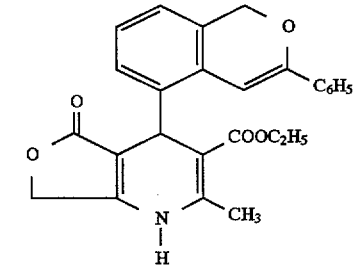

[E]
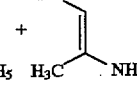

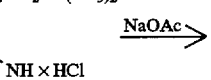

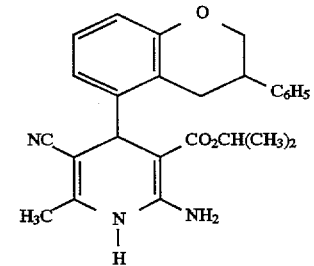

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric acid triamide or dimethylformamide, or acetic acid or halogenated hydrocarbons, such as methylene chloride or carbon tetrachloride, or hydrocarbons, such as benzene or toluene. It is also possible to use mixtures of the solvents mentioned. Preferred solvents are methanol, isopropanol, ethanol and n-propanol, acetonitrile or tetrahydrofuran, depending on the particular process variant [A], [B], [C] and [D].

The reaction temperatures can be varied within a relatively wide range. The reaction is in general carried out at between +10° C. and +150° C., preferably between +20° C. and +100° C., in particular at the boiling point of the particular solvent.

The reaction can be carried out under normal pressure, but also under increased or reduced pressure (for example 0.5 to 3 bar). The reaction is in general carried out under normal pressure.

Suitable chiral ester radicals are all the esters of enantiomerically pure alcohols, such as, for example, 2-butanol, 1-phenylethanol, lactic acid, lactic acid esters, mandelic acid, mandelic acid esters, 2-amino-alcohols, sugar derivatives, hydroxy amino acid derivatives and many other enantiomerically pure alcohols.

The diastereomers are in general separated either by fractional crystallization, by column chromatography or Craig partition. The optimum process must be decided upon from case to case, and it is sometimes also expedient to use combinations of the individual processes. Separation by crystallization or Craig partition or a combination of the two processes is particularly suitable.

The compounds of the general formula (II) in which $R^5$ represents the radical of the formula

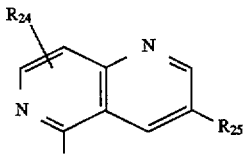

are known or can be prepared in a manner analogous to that in the literature.

The other compounds of the general formula (II) are new and can be prepared, for example, by a process in which

[I] in the case where $R^5=R^{5'}$ represents one of the radicals listed below:

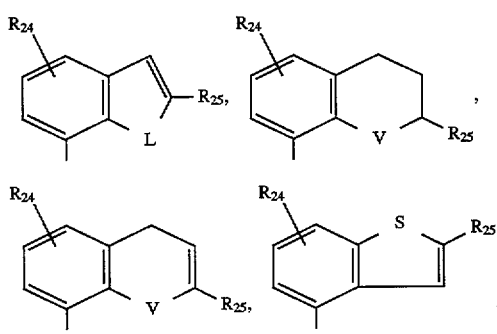

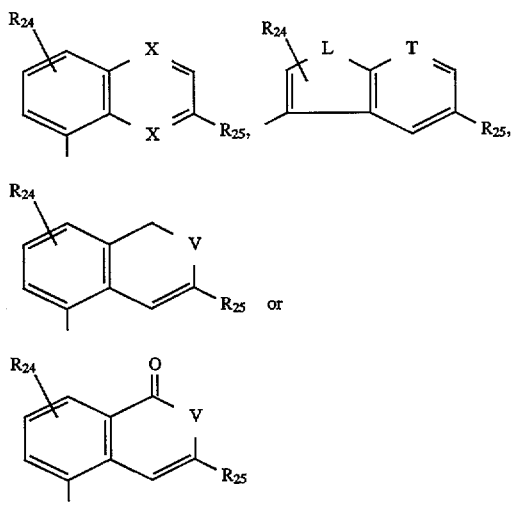

in which $R^{24}$, $R^{25}$, L, T, V and X have the abovementioned meaning, compounds of the general formula (XV)

$$R^{5'}-CO_2-R^{43} \qquad (XV)$$

in which $R^{5'}$ represents one of the abovementioned radicals and $R^{43}$ represents hydrogen or $C_1-C_4$-alkyl, are first converted with customary reducing agents, such as, for example, lithium aluminium hydride, or via a mixed anhydride with sodium borohydride, into the corresponding alcohols of the general formula (XVI)

$$R^{5'}-CH_2-OH \qquad (XVI)$$

in which $R^{5'}$ has the abovementioned meaning, and these are then oxidized, either after isolation or directly in situ, with oxidizing agents, such as, for example, manganese oxide, or

[II] in the case where $R^5$ represents the radical of the formula

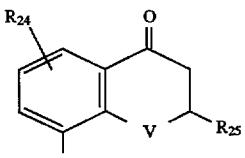

compounds of the general formula (XVII)

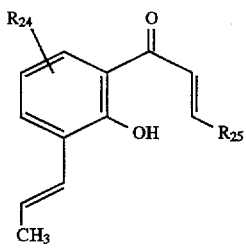 (XVII)

in which and $R^{24}$ and $R^{25}$ have the abovementioned meaning, are first cyclized by reaction with polyphosphoric acid in methylglycol to give the compounds of the general formula (XVIII)

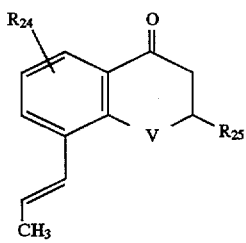 (XVIII)

in which $R^{24}$ and $R^{25}$ have the abovementioned meaning, and an ozonolysis is then carried out in one of the abovementioned solvents, preferably methylene chloride, or

[III] in the case where $R^5$ represents the radical of the formula

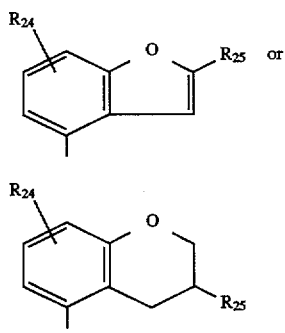

compounds of the general formula (XIX)

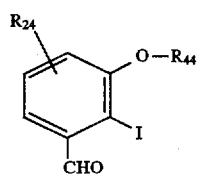 (XIX)

in which $R^{24}$ has the abovementioned meaning
and $R^{44}$ represents hydrogen, or represents a customary hydroxyl-protective group which can easily be split off, in case a) are reacted with compounds of the general formula (XX)

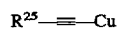 (XX)

in which $R^{25}$ has the abovementioned meaning, or in case b) are first reacted with compounds of the general formula (XXI)

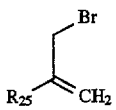 (XXI)

in which $R^{25}$ has the abovementioned meaning, and the products are then subjected to free radical cyclization, for example with tributyltin hydride/AIBN, and oxidation with $MnO_2$, or

[IV] in the case where $R^5$ represents the radical of the formula

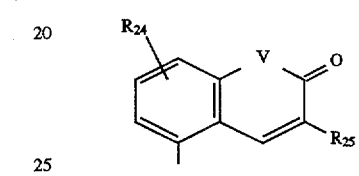

the corresponding alcoholates of the compounds of the general formula (XIX) are first reacted in the system $Pd(P(C_6H_5)_3)_2Cl$ with compounds of the general formula (XXII)

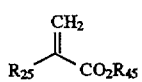 (XXII)

in which $R^{25}$ has the abovementioned meaning
and $R^{45}$ represents $C_1-C_4$-alkyl, to give the compounds of the general formula (XXIII)

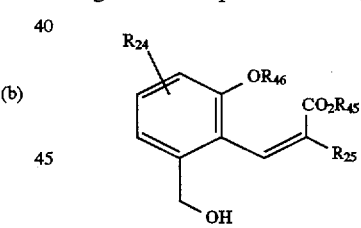 (XXIII)

in which $R^{24}$ and $R^{45}$ have the abovementioned meaning
and $R^{46}$ represents $C_1-C_4$-alkyl, and the products are then oxidized, as described above, with oxidizing agents, such as, for example, $MnO_2$, to give the corresponding aldehydes, which are cyclized in a last step with acids, such as boron tribromide, or

[IV] in the case where $R^5$ represents the radical of the formula

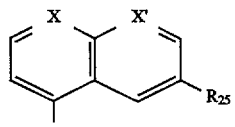

compounds of the general formula (XXIV)

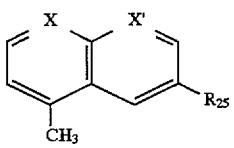

in which

X, X' and $R^{25}$ have the abovementioned meaning,
are oxidized with selenium dioxide in one of the abovementioned solvents, preferably dioxane,
or

[VI] in the case where $R^5$ represents the radical of the formula

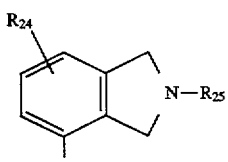

compounds of the general formula (XXV)

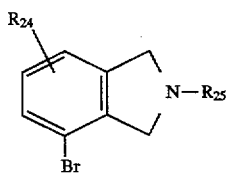

in which $R^{24}$ and $R^{25}$ have the abovementioned meaning,
are metallized with butyllithium under an inert gas atmosphere in one of the abovementioned solvents, preferably ether, and the products are then reacted with dimethylformamide,
or

[VII] in the case where $R^5$ represents the radical of the formula

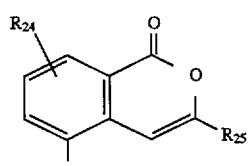

compounds of the general formula (XXVI)

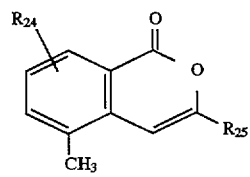

in which $R^{24}$ and $R^{25}$ have the abovementioned meaning,
are first brominated with N-bromosuccinimide, and the products are hydrolysed in a second step with potassium acetate/acetic acid, followed by sulphuric acid,
and, in the case of the N-oxides, starting from the corresponding compounds in which $R^5$ represents a nitrogen-containing ring, oxidation is first carried out with MCPBA and, if appropriate, the products are converted into the aldehydes, as described above,
and, if appropriate, the compounds of the general formula (I) are also varied by the oxidation or reduction types described above.

Suitable solvents for the individual steps are the above-mentioned solvents, preferably tetrahydrofuran or methylene chloride.

The reactions in general proceed in a temperature range from –20° C. to +150° C., preferably from 0° C. to 100° C., under normal pressure.

If appropriate, some reaction steps are carried out under an inert gas atmosphere.

The compounds of the general formula (XVI) are new in most cases and can be prepared, for example, as described above.

The compounds of the general formula (XV) are known in some cases or are new, but can then be prepared by customary methods.

The compounds of the general formulae (XVII), (XVIII), (XX), (XXI), (XXII), (XXIII), (XXXIV), (XXV) and (XXVI) likewise are known in some cases or are new, but can then be prepared by methods analogous to those known from the literature.

The acyl compounds of the general formula (III) and (X) are known or can be prepared by customary methods.

The compounds of the general formulae (V), (VI), (VIII), (VIIIa) and (XII) are known.

The ylidene compounds (IV), (VII) and (XI) are new, but can be prepared by customary methods.

The compounds of the general formula (IX) are new, but can be prepared by known methods, for example by a process in which benzylidene compounds of the general formula (IV) are reacted with chloroacetic acid esters and ammonium compounds.

The compounds of the general formula (XIII) are new and can be prepared as described above.

The above preparation processes are given merely for illustration. The preparation of the compounds of the formula (I) is not limited to these processes, but any modification of these processes can be used in the same manner for preparation of the compounds according to the invention.

The compounds according to the invention display an unforeseeable, valuable pharmacological action spectrum. They influence the contractility of the heart and the tone of the smooth muscle, and in particular they display calcium-antagonistic and calcium-agonistic actions. They can therefore be employed in medicaments for influencing pathologically changed blood pressure, as coronary therapeutics and for treatment of cardiac insufficiency. They can moreover be used for treatment of disturbances in cardiac rhythm, for lowering blood sugar, for detumescing mucosa and for influencing the salt and fluid balance.

The cardiac and vascular actions were found on the isolated perfused heart of the guinea-pig. The hearts of guinea-pigs weighing 250 to 350 g are used for this purpose. The animals are sacrificed by a blow on the head, the thorax is opened and a metal cannula is inserted into the exposed aorta. The heart is removed from the thorax with the lungs and connected via an aortic cannula to the perfusion apparatus with the perfusion running. The lungs are removed at the lung roots, and the perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), the $CaCl_2$ content of which is 1.2 mmol/l. 10 mmol/l of glucose are added as an energy-supplying substrate, and the solution is filtered free from particles before the perfusion. The solution is gassed with carbogen (95% $O_2$, 5% $CO_2$) to maintain the pH at 7.4. The hearts are perfused at a constant flow rate (10 ml/minute) at 32° C. by means of a roller squeeze pump.

To measure cardiac function, a latex balloon filled with liquid and connected to a pressure transducer via a column of liquid is inserted through the left auricle into the left ventricle and the isovolumetric contractions are recorded on a high-speed recorder. The perfusion pressure is recorded by means of a pressure transducer connected to the perfusion system before the heart. Under these conditions, a reduction in the perfusion pressure indicates coronary dilation and an increase or decrease in the left ventricular contraction amplitude indicates a reduction or, respectively, an increase in cardiac contractility. The compounds according to the invention are perfused in suitable dilutions into the perfusion system shortly before the isolated heart.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Administration is effected in the customary manner, preferably orally or parenterally, in particular perlingually or intravenously.

In general, it has proved advantageous in the case of intravenous administration to administer amounts of about 0.001 to 1 mg/kg, preferably about 0.01 to 0.5 mg/kg of body weight to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular as a function of the body weight or type of administration route, and of the behaviour of the individual towards the medicament, the nature of its formulation and the time or interval at which administration takes place. Thus, in some cases less than the abovementioned minimum amount may suffice, while in other cases the upper limit mentioned must be exceeded. Where relatively large amounts are administered, it may be advisable to divide these into several individual doses over the day.

Starting compounds

EXAMPLE I

8- Formyl-2-phenyl-imidazo [1.2-a]-pyridine

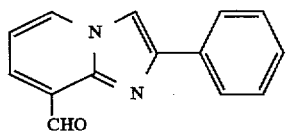

A mixture of 14.8 ml of dimethyl sulphoxide and 45 ml of methylene chloride is added dropwise to 8.7 ml (110 mmol) of oxalyl chloride in 220 ml of methylene chloride at −60° C. under inert conditions. 19.5 g (87 mmol) of 2-phenyl-8-hydroxymethyl-imidazo[1,2-a]pyridine in 90 ml of methylene chloride and 45ml of dimethyl sulphoxide are then added dropwise at −60° C., while stirring, and the mixture is stirred at −60° C. for 15 minutes end at −10° C. for 1 hour. 60.9 ml of triethylamine are now added and the mixture is stirred at −10° C. for 5 minutes and then allowed to come to room temperature. For working up, water is added, the organic phase is separated off and the aqueous phase is extracted twice more with methylene chloride. The combined organic phases are washed with saturated NaCl solution, dried over $Na_2SO_4$ and concentrated on a rotary evaporator. Stirring of the residue with ether gives 16.4 g of crystals (=73.8% of theory), which are chromatographed over silica gel for removal of chlorinated by-products.

Melting point: 96°–99° C.

MS: 222 (63%), 194 (100%), 102 (21%), 97 (15%)

EXAMPLE II

2-Cinnamoyl-6-propenylphenol

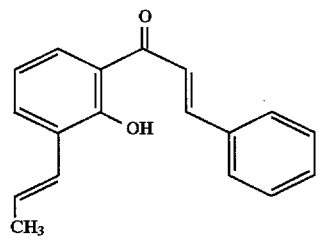

3.5 g (20 mmol) of 2-acetyl-6-(1-propenyl)phenol and 2.1 g (20 mmol) of benzaldehyde are dissolved in 20 ml of ethanol, 4 ml of concentrated NaOH are added, the mixture is stirred overnight, the red crystal slurry is diluted with methanol and acidified with concentrated HCl and, after cooling, the product is filtered off with suction. Orange-red crystals of melting point 95°–98° C. are obtained.

EXAMPLE III 8-(1-Propenyl)flavanone

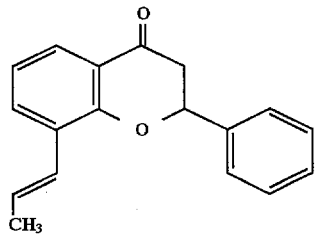

0.5 g of the compound from Example II is dissolved in 20 ml of methylglycol and the solution is boiled under reflux with 2 ml of polyphosphoric acid for 8 hours. The mixture is then precipitated in water and extracted with $CH_2Cl_2$, and unreacted Example I is separated off by chromatography. 70% of the title compound is obtained as a colourless oil, which later solidifies in wax-like form.

Melting point: <50° C.

EXAMPLE IV

Flavanone-8-carboxaldehyde

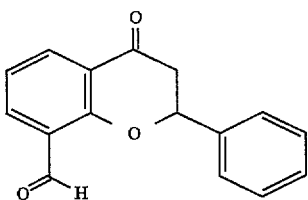

3.4 g (10 mmol) of the compound from Example III are subjected to ozonolysis in 50 ml of $CH_2Cl_2$ at −78° C. Customary working up gives 1.8 g of the title compound.

Melting point: 112°–113° C.

EXAMPLE V

Methyl 2-[(2,2-dimethoxy-1-phenylethyl)thio]benzoate

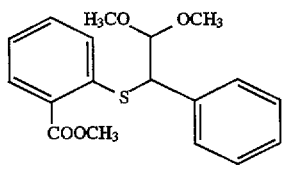

In each case 10 ml of methyl 2-mercaptobenzoate and 2-bromo-1,1-dimethoxy-2-phenylethane are refluxed overnight in 30 ml of methanol, with addition of 10 ml of NaOMe. After working up and purification by chromatography, 70% of viscous oil is obtained.

EXAMPLE VI

Methyl 2-phenylbenzo [b]thiophene-7-carboxylate

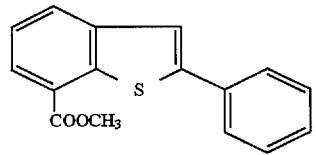

10 mmol of the compound from Example V are dissolved in 30 g of polyphosphoric acid and, after 20 minutes, the solution is poured onto water and the product is purified.

Yield: 85%

Melting point: 137°–140° C.

EXAMPLE VII

7-Hydroxymethyl-2-phenylbenzo [b]thiophene

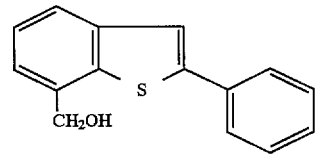

20 g of the compound from Example VI are dissolved in 75 ml of tetrahydrofuran and the solution is added dropwise to 40 mmol of $LiAlH_4$ in 50 ml of tetrahydrofuran. Customary working up gives 85% of the title compound.

Melting point: 125°–126° C.

EXAMPLE VIII

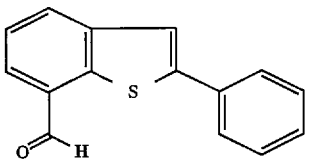

2-Phenyl-7-benzo [b]thiophenecarboxaldehyde 20 mmol of the compound from Example VII are boiled overnight with 100 mg of $MnO_2$ in 800 ml of $CH_2Cl_2$, the mixture is filtered with suction over kieselguhr and the filtrate is concentrated.

Yield: 90%

Melting point: 92°–94° C.

EXAMPLE IX

8-Hydroxymethyl-2-phenyl-3,4-dihydro-1(2H)-thiobenzopyran

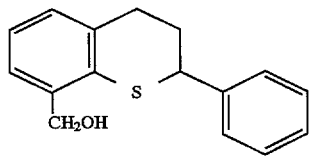

20.3 g of 8-hydroxymethyl-2-phenyl-4H-1-benzothiopyran (80 mmol) are dissolved in 400 ml of MeOH end 5 ml of glacial acetic acid end hydrogenated with 5 g of $PtO_2$ under 3 bar. The title compound is obtained as an oil, which is further reacted directly.

EXAMPLE X (±)2-Phenyl-3,4-dihydro-1(2H)-benzothiopyran-8-carboxaldehyde

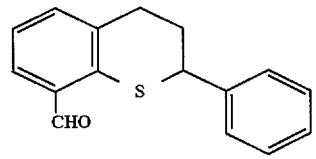

0.1 mol of the compound from Example IX are dissolved in 500 ml of $CH_2Cl_2$, the solution is refluxed overnight, with addition of 75 g of $MnO_2$, end filtered with suction, the filtrate is concentrated end the residue is crystallized with EtOH.

Melting point: 62°–63° C.

EXAMPLE XI

2-Phenyl-benzo[b]furan-7-carboxaldehyde

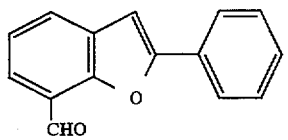

12 g of manganese dioxide are added to 2 g of 7-hydroxymethyl-2-phenylbenzo [b]furan (prepared according to Example 1 from EP 306 226) in 100 ml of methylene chloride and the mixture is heated under reflux for 1 hour. It is cooled end filtered with suction over a filtering auxiliary, and the filtrate is concentrated.

1.9 g of a colourless solid of melting point 60°–61° C. are obtained.

EXAMPLE XII

S-(2,3-Dimethylphenyl) N,N,N',N'-tetramethylphosphorodiamidothioate

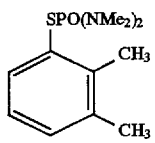

The preparation is carried out by a process analogous to a known process [M. Watanabe, M. Date, K. Kawanishi, R. Akiyoshi, S. Furukawa, J. Heterocyclic Chem. 1991, 28, 173] from 138 g (1 mol) of 2,3-dimethylthiophenol. Boiling point$_{0.3}$=150° C.

EXAMPLE XIII

S-(3-Methyl-2-phenacyl) phenyl N, N, N', N'-tetramethylphosphorodiamidothioate

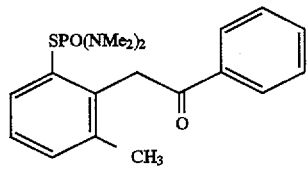

125 ml of a 1.4N solution of sec-BuLi in cyclohexane (175 mmol) are added dropwise to 20 g (73 mmol) of the compound from Example XII in 300 ml of absolute tetrahydrofuran. The mixture is stirred at −70° C. for 1 hour, and 18 ml of methyl benzoate are added dropwise. The mixture is allowed to come to room temperature and is introduced into a saturated ammonium chloride solution, the tetrahydrofuran content is evaporated off in vacuo, the mixture is extracted with ethyl acetate, the extract is dried and evaporated and the residue is chromatographed over silica gel (toluene→toluene/ethyl acetate 1:1)

Yield: 10.7 g (39% of theory)

Varying amounts of sec-butyl 2,3-dimethylphenyl thioether are obtained as a by-product.

EXAMPLE XIV

4-Methyl-2-phenylbenzo [b]thiophene

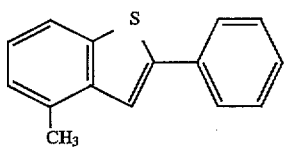

11 g (29.2 mmol) of the compound from Example XII are boiled under reflux in 50 ml of formic acid for 1 hour. The residue is neutralized with NaHCO$_3$ solution and extracted with ethyl acetate and the extract is chromatographed over silica gel. The by-product from Example XIII can be removed particularly easily at this stage by distillation under a high vacuum, the title compound remaining as a solid.

Yield: 5.0 g (76.3%)

Melting point: 83° C.

EXAMPLE XV

4-Acetoxymethyl-3-bromo-2-phenylbenzo [b]thiophene

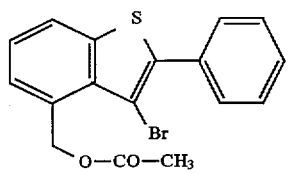

10 g (44.6 mmol) of the compound from Example XIV are boiled in 200 ml of CCl$_4$, under exposure to light, while a total of 24.1 g of N-bromosuccinimide, in addition to a spatula-tip of AIBN, are gradually added. After about 1 hour, the precipitate is filtered off and rinsed with CCl$_4$ and the solution is evaporated in vacuo. The residue (22.2 g) is boiled in 550 ml of glacial acetic acid with 22 g of potassium acetate for 3 hours. After the glacial acetic acid has been distilled off in vacuo, the residue is shaken with water and the mixture is extracted with ethyl acetate. Chromatography gives the title compound as the main product.

Yield: 4 g (25%)

EXAMPLE XVI

3-Bromo-4-hydroxymethyl-2-phenylbenzo [b]thiophene

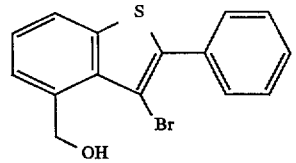

Hydrolysis of the compound from Example XV (1 g) in 100 ml of ethanol with 20 ml of 1N NaOH at room temperature gives, after 2 hours, 0.9 g of the title compound.

EXAMPLE XVII

4-Hydroxymethyl-2-phenyl-benzo [b]thiophene

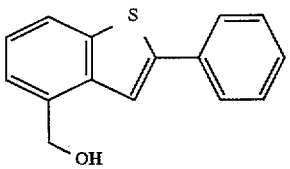

8.9 g (50.4 mmol) of PdCl$_2$ are added to 8 g (25.2 mmol) of the compound from Example XVI under argon in 160 ml of methanol at 0° C. 9.44 g (250 mmol) of NaBH$_4$ are then added in small portions. The hydrogen formed may ignite during this operation. The reaction proceeds highly exothermically; its conversion is monitored by means of HPLC. When the reaction has ended, the mixture is introduced into 1N HCl and extracted with ethyl acetate, the organic phase is evaporated on a rotary evaporator and the residue is chromatographed over silica gel.

Yield: 4.2 g (69%)

EXAMPLE XVIII

2-Phenyl-4-benzo [b]thiophene-carboxaldehyde

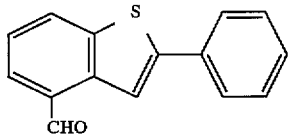

1 g (4.2 mmol) of the compound from Exhale XVII is boiled under reflux with 5 times the amount of MnO$_2$ in CHCl$_3$ for 2 hours.

Yield: 83%

EXAMPLE XIX

2-Phenyl-4-benzo [b]furan-carboxaldehyde

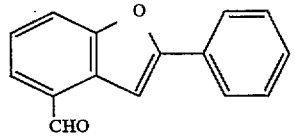

14.9 g (60 mmol) of 3-hydroxy-2-iodo-benzaldehyde are stirred with 10.4 g (63.2 mmol) of copper phenylacetylide in 300 ml of pyridine at 120° C. for 3 hours. The mixture is concentrated and the residue is chromatographed over a silica gel column to give 12.4 g (93%) of the title compound.

Melting point: 103° C.

R$_f$ (silica gel, toluene): 0.38

EXAMPLE XX

2-Iodo-3-[(2-phenyl-2-propenyl)oxy]benzaldehyde

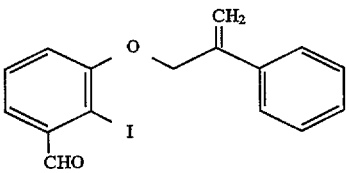

6.72 g (0.28 mmol) of sodium hydride are dissolved in 660 ml of ether and 120 ml of dimethylformamide under argon, and 64.1 g (0.26 mol) of 3-hydroxy-2-iodobenzaldehyde in 65 ml of ether are slowly added. After the mixture has been stirred at room temperature for 15 minutes, 61 g (0.28 mol) of 3-bromo-2-phenyl-1-propene, dissolved in 60 ml of ether, are added dropwise and the mixture is stirred overnight.

Yield: 55.5 g (59%).

Melting point: 88° C.

EXAMPLE XXI

5-Hydroxymethyl-3-phenyl-1(2H)-dihydrobenzopyran

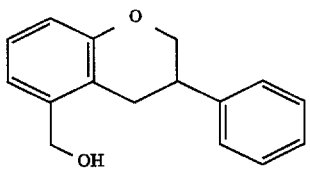

55.5 g (152 mmol) of the compound from Example XX in 3 l of benzene, 150 ml (553 mmol) of tributylstannane and 200 mg of AIBN are heated under reflux under argon for 2 hours. The mixture is shaken with water and dilute hydrochloric acid and extracted with ethyl acetate and the extract is evaporated on a rotary evaporator. After standing overnight, the alcohol of the title compound is essentially present, and can be crystallized out by addition of pentane and separated off from the organotin compounds.

EXAMPLE XXII

3-Phenyl-1(2H)-dihydrobenzo-pyran-5-carboxyaldehyde

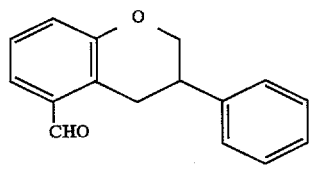

36 g of the alcohol of the compound from Example XXI are boiled with 120 g of MnO$_2$ in chloroform for 1 hour, the mixture is filtered with suction over kieselguhr and the filtrate is evaporated on a rotary evaporator. 27 g (75%) of the title compound are obtained as an oil.

EXAMPLE XXIII

Ethyl 3-(3-hydroxymethyl-1-methoxy-2-phenyl)-2-phenyl-2-propenoate

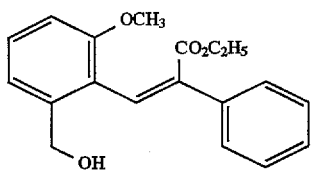

13.3 g (50.4 mmol) of 3-hydroxymethyl-2-iodo-1-methoxybenzene, 8.87 g (50.4 mmol) of ethyl atropate and 7.05 ml of triethylamine are dissolved in 600 ml of dimethylformamide and the solution is saturated with argon. 350 mg of palladium bis(triphenylphosphine) dichloride are then added and the mixture is stirred overnight at 140° C. The black solution is evaporated in vacuo and the residue is chromatographed over silica gel. 7.1 g (45%) of the title compound are obtained.

EXAMPLE XXIV

Ethyl-3-(3-formyl-1-methoxy-2-phenyl)-2-Phenyl-2-propenoate

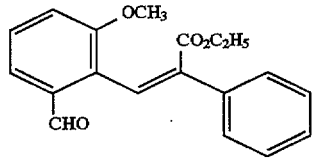

16.9 g (54 mmol) of the compound from Example XXIII in 350 ml of chloroform are boiled with 85 g of manganese dioxide for 3 hours. The mixture is filtered through kieselguhr and the filtrate is evaporated in vacuo.

Yield: 16.7 g (99%)

EXAMPLE XXV

3-Phenyl-5-coumarin-carboxaldehyde

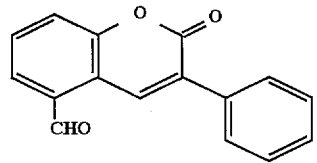

110 ml of a 1M solution of $BBr_3$ in methylene chloride are added to 22.2 g (71.5 mmol) of the compound from Example XXIV in 500 ml of methylene chloride at 0° C. The mixture is stirred first at 0° C. for 2 hours and then at room temperature for 2 hours. It is hydrolysed in an excess of aqueous $K_1HPO_4$ solution for 1.5 hours, while stirring. The organic phase gives a mixture, from which 2.5 g (14%) of the title compound can be isolated by chromatography. The title compound shows characteristic luminescence in thin layer chromatography with fluorescence indicator at 366 nm.

MS (EI): 250 (100%), 221 (18%), 165 (15%)

EXAMPLE XXVI

6-Phenyl-4-quinoline-carboxaldehyde

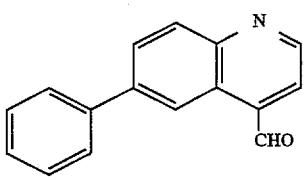

1.4 ml of water and 17 g of selenium dioxide are added to 8.5 g (38.8 mmol) of 4-methyl-6-phenyl-quinoline in 85 ml of dioxane and the mixture is boiled for 1 hour. The selenium is filtered off with suction and washed with methanol and the filtrate is concentrated. The resulting mixture is separated by flash chromatography, the clean fractions are concentrated and the residue is stirred with ether, filtered off with suction and washed with ether. 3.2 g of colourless crystals of melting point 115° C. are obtained.

EXAMPLE XXVII

2-Phenyl-isoindoline-4-carboxaldehyde

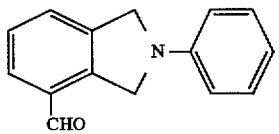

2.3 ml (3.7 mmol) of a 1.6 molar solution of butyllithium in hexane are added to 14 ml of dry ether in a dry apparatus under argon. A solution of 930 mg (3.4 mmol) of 4-bromo-2-phenylisoindoline in 10 ml of dry ether is then added dropwise at −70° C. The mixture is stirred at −70° C. for 30 minutes, and 0.3 ml of dry dimethylformamide in 0.5 ml of ether is added. The mixture is stirred at 70° C. for 3 hours and heated to −5° C., and 13.6 ml of 1N hydrochloric acid are added dropwise. 50 ml of ether are added and the mixture is separated. The aqueous phase is extracted by shaking with ether and the combined ether phases are washed once with water, dried and concentrated. 600 mg of yellowish crystals of melting point 120°–122° C. are obtained.

EXAMPLE XXVIII

3-Phenyl-5-quinoxalinecarboxylic acid

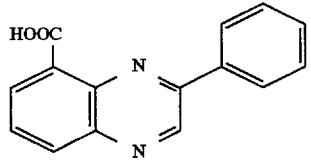

30 g (164.8 mmol) of 2-amino-3-nitrobenzoic acid are suspended in 900 ml of ethanol, 6 g of 5% strength Pd-on-charcoal are added and hydrogenation is carried out under 3 bar in a Parr apparatus for about 2 hours, until the uptake of hydrogen has ended. The catalyst is filtered off over kieselguhr and 12.8 g (83 mmol) of phenylglyoxal hydrate are added to the solution. The mixture is then stirred at room temperature under nitrogen for 2.5 hours, and the precipitate formed is filtered off with suction, rinsed with ethanol and dried.

EXAMPLE XXIX

5-Hydroxymethyl-3-phenylquinoxaline

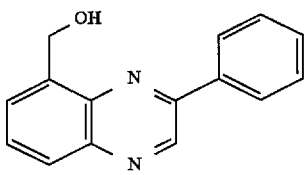

14.5 g (58 mmol) of the compound from Example XXVIII in 150 ml of tetrahydrofuran are initially introduced into the reaction vessel at 0° C. under nitrogen. A solution of 11 g (290 mmol) of LiAlH₄ in 60 ml of tetrahydrofuran is now added dropwise, stirring, and the mixture is subsequently stirred at room temperature for a maximum of a further 1 hour, monitoring by thin layer chromatography. It is then hydrolysed by dropwise addition of water and the pH is brought to 5 with dilute hydrochloric acid. After extraction with ethyl acetate and drying of the organic phase over $Na_2SO_4$, the title compound is obtained in a 58% yield and is further reacted directly.

MS (EI): 236 ($M^+$, 100%), 207 (41%)

EXAMPLE XXX

3-Phenyl-quinoxaline-5-carboxaldehyde

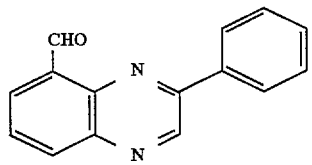

16.3 g (69 mmol) of the compound from Example XXIX are dissolved in 350 ml of chloroform, 40 g of $MnO_2$ are added and the mixture is boiled under reflux for 2 hours. A further 16 g of $MnO_2$ is then added and the mixture is boiled overnight. The $MnO_2$ is filtered off and the filtrate is concentrated on a rotary evaporator to give, after chromatography of the residue over silica gel (mobile phase toluene: ethyl acetate 4:1), the title compound in 66% yield.

Melting point: 149° C.

EXAMPLE XXXI

Methyl 5-phenyl-3-thieno [2,3-b] pyridinecarboxylate

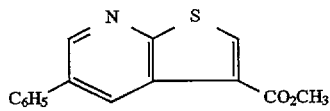

54.9 g (0.32 mmol) of methyl 2-nitro-4-thiophenecarboxylate are dissolved in 1373 ml of methanol, and 1373 ml of concentrated hydrochloric acid, followed by 109.8 g of tin granules, are added. The mixture is stirred with a precision glass stirrer for 1½–3 hours and the conversion is monitored by means of thin layer chromatography (neutralize sample beforehand). The reaction time depends on the stirring speed. When no further educt is present in the mixture, the tin granules which remain are filtered off. A solution of 54.9 g (0.37 mol) of 2-phenylmalonaldehyde in 500 ml of methanol is then added and the mixture is stirred at room temperature for 1.5 hours. The Schiff's base intermediately formed is detectable on the thin layer chromatogram as a yellow spot. The mixture is then boiled under reflux for 2.5 hours, the cooled solution is extracted with methylene chloride, dried and evaporated on a rotary evaporator and the residue is chromatographed over silica gel.

Yield: 39 g (45.3%)

$R_f$ (silica gel, toluene/ethyl acetate 1:1)=0.59

EXAMPLE XXXII AND EXAMPLE XXXIII

3-Hydroxymethyl-5-phenylthieno [2,3-b]pyridine (XXXII)

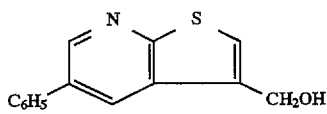

5-Phenyl-3-thieno[2,3-b]pyridinecarboxaldehyde (XXXIII)

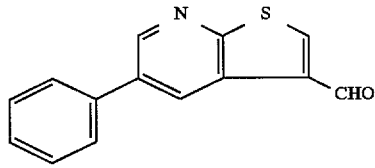

39 g (0.145 mol) of the compound from Example XXXI are dissolved in 350 ml of tetrahydrofuran, and 9.1 g of lithium aluminium hydride in 300 ml of tetrahydrofuran are added dropwise at 0° C. under argon, while stirring. The mixture is allowed to come to room temperature and is stirred for a further hour. It is then hydrolysed carefully with water, while cooling with ice, acidified to pH 3–4 with HCl and extracted 3 times with ethyl acetate. After the solvent has been evaporated off in vacuo, 28.3 g of the compound from Example XXXII are obtained and are dissolved in 600 ml of chloroform, 280 g of maganese dioxide are added and the mixture is boiled under reflux for 5 hours. It is filtered over kieselguhr, the filtrate is evaporated on a rotary evaporator and the residue is chromatographed over a short silica gel column. The compound from Example XXXIII is obtained in a yield of 20.0 g (60%). $R_f$(silica gel, toluene/ ethyl acetate 1:1)=0.69

MS (EI): 239 (100%), 210 (15%), 152 (10%), 139 (15%)

Yield: 89% (based on the phenylglyoxal)

MS (EI): 250 ($M^+$, 6%), 206 (M—$CO_2$, 100%), 103 (12%), 76 (15%)

EXAMPLE XXXIV

5-Dibromomethyl-3-phenylisocoumarin

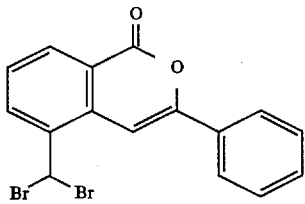

29.2 g (124 mmol) of 5-methyl-3-phenyl-isocoumarin are boiled in 1 l of carbon tetrachloride with 55 g of N-bromosuccinimide and a catalytic amount of AIBN for 10 hours, a further 22 g of N-bromosuccinimide and a little AIBN being added in each case after 3 and 6 hours. After cooling, 60 g of silica gel are added to the mixture, the solvent is evaporated off in vacuo and the residue is chromatographed over a silica gel column (toluene).

Yield: 47 g (96%)

Melting point: 197° C.

$R_f$ (dibromide, monobromide, educt): 0.24, 0.28, 0.34

EXAMPLE XXXV 3-phenyl-5-isocoumarincarboxaldehyde

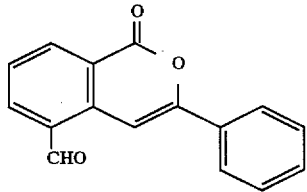

23.5 g (60 mmol) of the compound from Example XXXIV are boiled in 250 ml of glacial acetic acid with 23.5 g of potassium acetate for 3 hours. The mixture is then poured onto water and neutralized with $NaHCO_3$. It is extracted three times by shaking with methylene chloride, dried and concentrated. The resulting product is dissolved in dioxane and, after addition of 2N $H_2SO_4$, the mixture is stirred at 50° C. for 2 hours. It is extracted by shaking with methylene chloride and the dried and concentrated organic phase is chromatographed.

Yield: 11.5 g (77%)

Melting point: 154° C.

MS (DCI): 251 (100%, M+H), 105 (80%)

EXAMPLE XXXVI

3-Phenyl-5-isocomarincarboxaldehyde dimethyl acetal

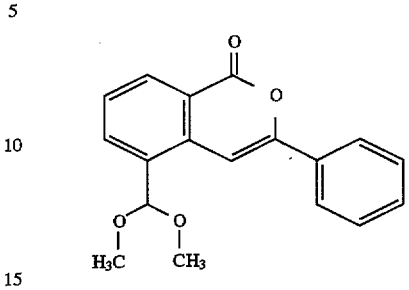

10 ml of concentrated HCl are added to 8 g (32 mmol) of the compound from Example XXXV in 30 ml of methanol and the mixture is stirred at room temperature for 3 hours. It is concentrated to one third of the volume and the crystals which have precipitated are filtered off with suction.

Yield: 8.3 g (88%)

$R_f$ (toluene/ethyl acetate=4:1): 0.53

MS (EI): 296 ($M^+$, 68%), 265 (100%)

EXAMPLE XXXVII and XXXVIII

3-Phenyl-5-isochromenecarboxaldehyde dimethyl acetal

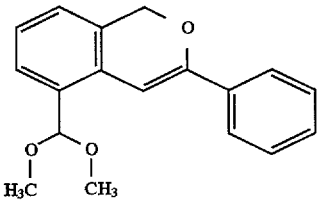

(XXXVII)

5-Hydroxymethyl-1-methoxy-3-phenylisochromene

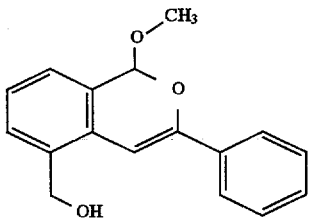

(XXXVIII)

A solution of 2.5 g of $LiAlH_4$ in 400 ml of ether is slowly added dropwise to 8 g (27 mmol) of the compound from Example XXXVI in 400 ml of ether at 0° C. The mixture is stirred at room temperature for 30 minutes and hydrolysed carefully with water. The ether phase which has been separated off is evaporated in vacuo and the residue is chromatographed.

$R_f$ (toluene/ethyl acetate 4:1)=0.25

EXAMPLE XXXVIII

MS (DCl, $NH_3$): 269 ($M^+$+1, 100%), 251 (45%), 237 (20%), 105 (30%)

EXAMPLE XXXIX

3-Phenyl-5-isochromenecarboxaldehyde

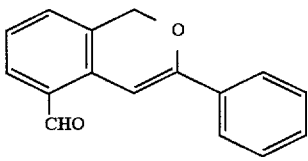

10 g of the mixture from Examples XXXVII and XXX-VIII are dissolved in 50 ml of dioxane, 60 ml of 1N HCl are added and the mixture is stirred vigorously for 10 minutes.

$R_f$ (toluene/ethyl acetate 4:1): 0.4 (yellow fluorescence)

Melting point: 141° C.

MS (EI): 236 (M+, 68%), 207 (43%), 179 (18%), 105 (100%), 77 (54%)

Preparation Examples

EXAMPLE 1

Ethyl 5-cyano-1,4-dihydro-2,6-dimethyl-4-(2-phenyl-4H-1-benzothiopyran-8-yl)-3-pyridinecarboxylate

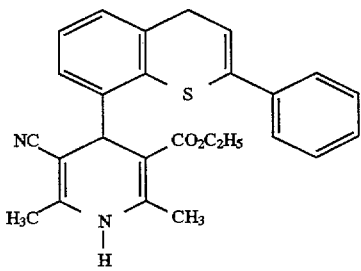

3 mmol of Ethyl 5-cyano-1,4-dihydro-2,6-dimethyl-4-(4-oxo-2-phenyl-4H-1-benzothiopyran-8-yl)-3-pyridinecarboxylate (DE 33 11 005) and 15 mmol of NaBH$_4$ are initially introduced into 10 ml of t-butanol, 1.8 ml of MeOH are added at 60° C. and the mixture is kept at 65° C. for 8 hours. Customary working up gives the title compound.

Melting point: 206°–207° C.

EXAMPLE 2

Ethyl 5-cyano-1,4-dihydro-2,6-dimethyl-4-(3-phenyl-1,8-naphthyridin-5-yl)pyridine-3-carboxylate

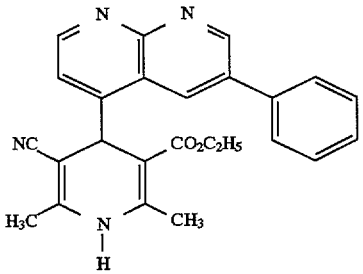

2 g (8.54 mmol) of 3-phenyl-1,8-naphthyridine-5-carboxaldehyde, 0.7 g (8.54 mmol) of 3-aminocrotononitrile and 1.08 ml of ethyl acetoacetate (8.54 mmol) are boiled in 16 ml of ethanol in an N$_2$ atmosphere for 16 hours. Chromatography over silica gel and elution with ethyl acetate gives 0.38 g (10.8% of theory) of the title compound of melting point 265° C.

The examples listed in Table 1 are prepared analogously to the instructions of Example 1:

TABLE 1

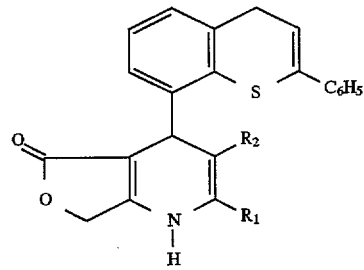

| Ex. No. | R$^1$ | R$^2$ | Melting point °C. |
|---|---|---|---|
| 3 | —CH$_3$ | —CO$_2$C$_2$H$_5$ | amorphous |
| 4 | —CH$_3$ | —CO$_2$CH$_3$ | 260 (decomposition) |
| 5 | —CH$_3$ | —CO$_2$C$_2$H$_5$ | |

The examples listed in Tables 2–19 are prepared analogously to the instructions of Example 2:

TABLE 2

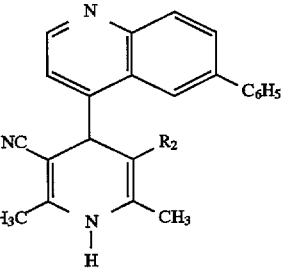

| Ex. No. | R$^2$ | Melting point °C. |
|---|---|---|
| 6 | —CO$_2$—CH(CH$_3$)$_2$ | 189–191 |
| 7 | —CO$_2$C$_2$H$_5$ | 209 |

TABLE 3

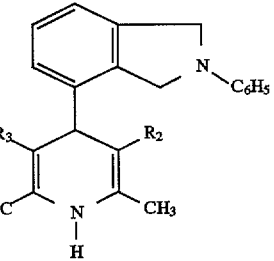

| Ex. No. | R$^2$ | R$^3$ | Melting point °C. |
|---|---|---|---|
| 8 | —CO$_2$—CH(CH$_3$)$_2$ | —CN | 194–197 |
| 9 | —CO$_2$CH$_3$ | —NO$_2$ | 208 |
| 10 | —CO$_2$(CH$_2$)$_2$—C$_2$H$_5$ | —CN | 221 |
| 11 | —CO$_2$—CH(CH$_3$)$_2$ | —NO$_2$ | 135 |

TABLE 4

[Structure: dihydropyridine with thiochroman-C6H5 substituent]

| Ex. No. | R² | R³ | R⁴ | Melting point °C. |
|---|---|---|---|---|
| 12 | —CO₂C₂H₅ | | (lactone) | 244–248 |
| 13 | —CO₂CH₃ | | (lactone) | 255 |
| 14 | —CO₂C₂H₅ | —NO₂ | —CH₃ | 160–163 |
| 15 | —CO₂CH₃ | —NO₂ | —CH₃ | 210–212 (decomposition) |
| 16 | —CO₂(CH₂)₂OCH₃ | | (lactone) | 199 |
| 17 | —CO₂—CH(CH₃)₂ | | (lactone) | 239 |
| 18 | —CO₂—CH(CH₃)₂ | —CN | —CH₃ | 142–143 |
| 19 | —CO₂C₂H₅ | —CN | —CH₃ | 193–195 |
| 20 | —CO₂C₂H₅ | —CN | —CH₃ | 96 amorphous |

TABLE 5

[Structure: dihydropyridine with benzofuran-C6H5 substituent]

| Ex. No. | R² | R³ | R⁴ | Melting point °C. |
|---|---|---|---|---|
| 21 | —CN | —CN | —CH₃ | 231 |
| 22 | —CO₂(CH₂)₂CH₃ | —CN | —CH₃ | 181 |
| 23 | —CO₂—CH(CH₃)₂ | | (lactone) | 201 |
| 24 | —CO₂—CH(CH₃)₂ | —NO₂ | —CH₃ | 201 |
| 25 | —CO₂—CH(CH₃)₂ | —CN | —CH₃ | 201 |
| 26 | —CO₂C₂H₅ | | (lactone) | 250 |

TABLE 6

[Structure: dihydropyridine with chromanone-C6H5 substituent]

| Ex. No. | R² | R³ | R⁴ | Melting point °C. |
|---|---|---|---|---|
| 27 | —CO₂—C₂H₅ | | (lactone) | 137 (decomposition) |
| 28 | —CO₂—C₂H₅ | —NO₂ | —CH₃ | 150 |
| 29 | —CO₂C₂H₅ | —CN | —CH₃ | 177 |

TABLE 7

| Ex. No. | R¹ | R² | R³ | R⁴ | Melting point °C. |
|---|---|---|---|---|---|
| 30 | —NH₂ | —CO₂—CH(CH₃)₂ | —CN | —CH₃ | 258 |
| 31 | —CH₃ | —CO₂—CH(CH₃)₂ | —CN | —CH₃ | 187 |
| 32 | —CH₃ | CN | —CN | —CH₃ | 223 |
| 33 | —CH₃ | —CO₂—CH(CH₃)₂ | —C(=O)O—CH₂CH₃ | | 233 |
| 34 | —CH₃ | —CO₂—CH(CH₃)₂ | —NO₂ | —CH₃ | 233 |
| 35 | —CH₂—CO₂CH₃ | —CO₂C₂H₅ | —CO₂—CH(CH₃)₂ | —CH₃ | 156 |

TABLE 8

| Ex. No. | R¹ | R² | R³ | R⁴ | Melting point °C. |
|---|---|---|---|---|---|
| 36 | —CH₃ | —CO₂C₂H₅ | —NO₂ | —CH₃ | 263 |
| 37 | —CH₃ | —CO₂—CH(CH₃)₂ | —CN | —CH₃ | 250 |
| 38 | —CH₃ | —CO₂C₂H₅ | —C(=O)O—CH₂CH₃ | | 239 |
| 39 | —CH₃ | —CO₂CH₃ | —C(=O)O—CH₂CH₃ | | 226 |
| 40 | —CH₃ | —CO₂—CH(CH₃)₂ | —NO₂ | —CH₃ | 234 |
| 41 | —CH₃ | —CO₂—CH(CH₃)₂ | —C(=O)O—CH₂CH₃ | | 270 |

TABLE 8-continued
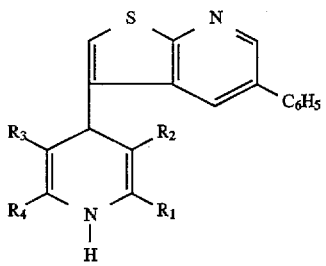
| Ex. No. | R¹ | R² | R³ | R⁴ | Melting point °C. |
|---|---|---|---|---|---|
| 42 | —CH₃ | —CO₂—CH(CH₃)₂ | —CO₂(CH₂)₂OCH₃ | —CH₃ | 165–167 |
| 43 | —CH₃ | —CN | 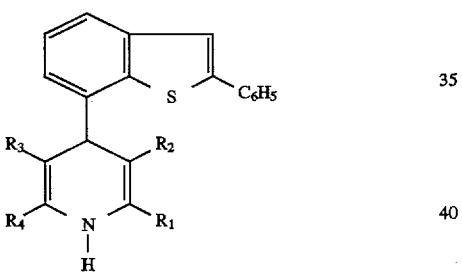 | | 265 |
| 44 | —NH₂ | —CO₂—CH(CH₃)₂ | —CN | —CH₃ | 240 |
| 45 | —CH₃ | —CO₂CH₂CO₂H | —CN | —CH₃ | 212 |
| 46 | —CH₃ | —CO₂(CH₂)₂OCH₃ | —CO₂(CH₂)₂OCH₃ | —CH₃ | 174–176 |
| 47 | —CH₃ | —CO₂C₂H₅ | —CN | —CH₃ | 220 |
TABLE 9
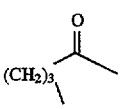
| Ex. No. | R¹ | R² | R³ | R⁴ | Melting point °C. |
|---|---|---|---|---|---|
| 48 | —CH₃ | —CO₂C₂H₅ | —NO₂ | —CH₃ | foam |
| 49 | —CH₃ | —CO₂C₂H₅ | 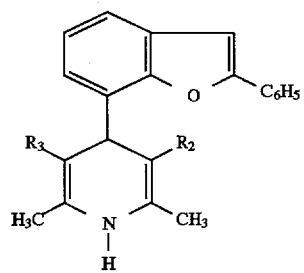 | | foam |
| 50 | —CH₃ | —CO₂C₂H₅ | —CN | —CH₃ | 240 |
TABLE 10
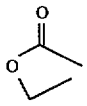
| Ex. No. | R² | R³ | Melting point °C. |
|---|---|---|---|
| 51 | —CO₂C₂H₅ | —CN | 217 |
| 52 | —CO₂—CH(CH₃)₂ | —CN | 210 |
| 53 | —CO₂CH₃ | —NO₂ | 228 |

TABLE 11
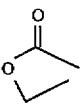
| Ex. No. | R¹ | R² | R³ | R⁴ | R' | Melting point °C. |
|---|---|---|---|---|---|---|
| 54 | —CH₃ | —CO₂C₂H₅ | —CN | —CH₃ | -o-Cl | 213 |
| 55 | —CH₃ | —CO₂C₂H₅ | —CN | —CH₃ | -m-Cl | 222 |
| 56 | —CH₃ | —CO₂C₂H₅ | 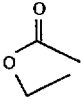 | | -o-F | 140 |
| 57 | —CH₃ | —CO₂C₂H₅ | —NO₂ | —CH₃ | -o-F | 182 |
| 58 | —CH₃ | —CO₂C₂H₅ | —CN | —CH₃ | -o-F | 189 |
| 59 | —CH₃ | —CO₂CH₃ | 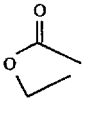 | | H | 282 |
| 60 | —CH₃ | —CO₂—CH(CH₃)₂ | 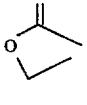 | | H | 237 |
| 61 | —CH₃ | —CO₂—(CH₂)₂OCH₃ | 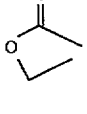 | | H | 119–120 (decomposition) |
| 62 | —CH₃ | —CO₂C₂H₅ | 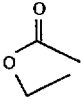 | | H | 245 |
| 63 | —CH₃ | —CO₂C₂H₅ | —CN | —CH₃ | H | 216 |
| 64 | —CH₃ | —CO₂C₂H₅ | —NO₂ | —CH₃ | —CH₃ | 209 |

TABLE 12
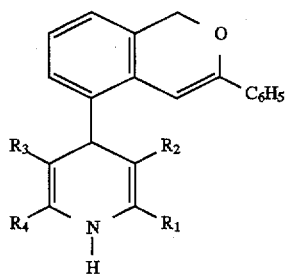
| Ex. No. | R¹ | R² | R³ | R⁴ | Melting point °C. |
|---|---|---|---|---|---|
| 65 | —CH₃ | —CO₂C₂H₅ | —NO₂ | —CH₃ | 257 |
| 66 | —CH₃ | —CO₂CH(CH₃)₂ | —CN | —CH₃ | 140 |
| 67 | —CH₃ | —CO₂CH(CH₃)₂ | 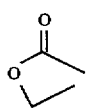 | | 240 |
TABLE 12-continued
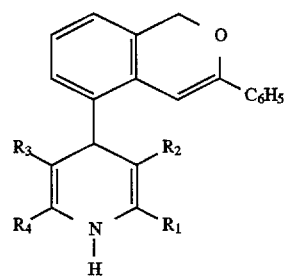
| Ex. No. | R¹ | R² | R³ | R⁴ | Melting point °C. |
|---|---|---|---|---|---|
| 68 | —CH₃ | —CN | —CN | —CH₃ | 100 |
| 69 | —CH₃ | —CO₂C₂H₅ | 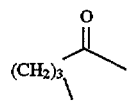 | | 249 |
TABLE 13
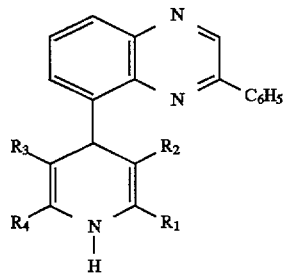
| Ex. No. | R¹ | R² | R³ | R⁴ | Melting point °C. |
|---|---|---|---|---|---|
| 70 | —CH₃ | —CO₂C₂H₅ | —NO₂ | CH₃ | 245 (decomposition) |
| 71 | —CH₃ | —CO₂C₂H₅ |  | | 277 |
| 72 | —CH₃ | —CO₂CH₃ |  | | 282 (decomposition) |
| 73 | —CH₃ | —CO₂C₂H₅ |  | | 265 (decomposition) |

TABLE 13-continued

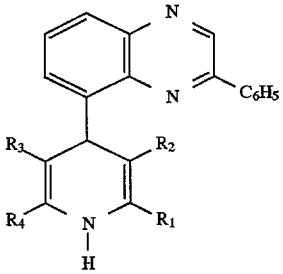

| Ex. No. | R¹ | R² | R³ | R⁴ | Melting point °C. |
|---|---|---|---|---|---|
| 74 | —CH₃ | —CO₂CH(CH₃)₂ |  | | 266 |
| 75 | —CH₃ | —CO₂CH(CH₃)₂ | —CN | —CH₃ | 230 |
| 76 | —CH₃ | —CO₂CH₃ | —CN | —CH₃ | 252 |
| 77 | —CH₃ | —CO₂CH(CH₃)₂ | —NO₂ | —CH₃ | 228 |
| 78 | —CH₃ | —CO₂C₂H₅ | —CN | —CH₃ | 270 |
| 79 | —CH₃ | —CO₂CH₃ | —CO—NH—◁ | —CH₃ | 150 |

TABLE 14

| Ex. No. | R¹ | R² | R³ | R⁴ | Melting point °C. |
|---|---|---|---|---|---|
| 80 | —CH₃ | —CO₂CH(CH₃)₂ | —CN | —CH₃ | amorphous foam* |
| 81 | —CH₃ | —CO₂CH(CH₃)₂ | —NO₂ | —CH₃ | amorphous foam* |
| 82 | —CH₃ | —CO₂CH(CH₃)₂ | 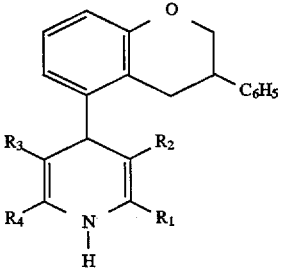 | | amorphous foam* |
| 83 | —CH₃ | —CO₂CH(CH₃)₂ | —CN | —NH₂ | amorphous foam* |
| 84 | —CH₃ | —CN | —CN | —CH₃ | amorphous foam |

* = diastereomer mixture

TABLE 15

| Ex. No. | R¹ | R² | R³ | R⁴ | Melting point °C. |
|---|---|---|---|---|---|
| 85 | —CH₃ | —CO₂CH(CH₃)₂ | —CO₂C₂H₅ | —CH₂—O—CO—CH₃ | 166 |
| 86 | —CH₃ | —CO₂CH(CH₃)₂ | | (lactone ring) | 170 |
| 87 | —CH₃ | —CN | —CN | —CH₃ | 261 |

TABLE 16

| Ex. No. | R¹ | R² | R³ | R⁴ | Melting point °C. |
|---|---|---|---|---|---|
| 88 | —CH₃ | —CO₂CH(CH₃)₂ | —CO₂C₂H₅ | —CH₂—O—CO—CH₃ | 270 |
| 89 | —CH₃ | —CO₂C₂H₅ | —CO₂C₂H₅ | —CH₂—O—CO—CH₃ | 186 |
| 90 | —CH₃ | —CO₂—C₂H₅ | | (lactone ring) | 272 |
| 91 | —CH₃ | —CO₂CH(CH₃)₂ | —CN | —CH₃ | 222 |
| 92 | —CH₃ | —CO₂(CH₂)₂CH₃ | —CN | —CH₃ | 218 |
| 93 | —CH₃ | —CO₂C₂H₅ | —CN | —CH₃ | 242 |
| 94 | —CH₃ | —CO₂CH₃ | —NO₂ | —CH₃ | 188 |
| 95 | —CH₃ | —CO₂CH(CH₃)₂ | | (lactone ring) | 270 |

TABLE 17
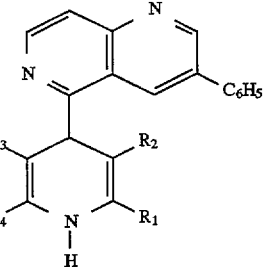
| Ex. No. | R¹ | R² | R³ | R⁴ | Melting point °C. |
|---|---|---|---|---|---|
| 96 | $-CH_3$ | $-CO_2CH(CH_3)_2$ | $-CO_2C_2H_5$ | $-CH_2-O-CO-CH_3$ | 195 |
| 97 | $-CH_3$ | $-CO_2C_2H_5$ | $-CN$ | $-CH_2-O-CO-CH_3$ | 208 |
| 98 | $-CH_3$ | $-CO_2CH(CH_3)_2$ | $-CN$ | $-CH_3$ | 235 |
| 99 | $-CH_3$ | $-CO_2(CH_2)_2CH_3$ | $-CN$ | $-CH_3$ | 251 |
| 100 | $-CH_3$ | $-CO_2C_2H_5$ | $-CN$ | $-CH_3$ | 243 |
| 101 | $-CH_3$ | $-CO_2C_2H_5$ |  | | 285 |
| 102 | $-CH_3$ | $-CO_2CH(CH_3)_2$ |  | | 267 |
TABLE 18
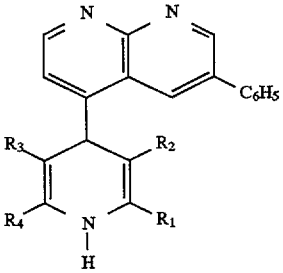
| Ex. No. | R¹ | R² | R³ | R⁴ | Melting point °C. |
|---|---|---|---|---|---|
| 103 | $-CH_3$ | $-CO_2C_2H_5$ | $-NO_2$ | $-CH_3$ | 282 |
| 104 | $-CH_3$ | $-CO_2CH(CH_3)_2$ | $-NO_2$ | $-CH_3$ | 280 |
| 105 | $-CH_3$ | $-CO_2CH_3$ |  | | 205 |
| 106 | $-CH_3$ | $-CO_2CH(CH_3)_2$ |  | | 258 |
| 107 | $-CH_3$ | $-CO_2C_2H_5$ |  | | 268 |

TABLE 18-continued

| Ex. No. | R¹ | R² | R³ | R⁴ | Melting point °C. |
|---|---|---|---|---|---|
| 108 | —CH₃ | —CO₂CH₃ | —CN | —CH₃ | 255 |
| 109 | —CH₃ | —CO₂CH₃ | —CO—NH—◁ | —CH₃ | 230 (decomposition) |
| 110 | —CH₃ | —CO₂CH(CH₃)₂ | —CN | —CH₃ | 269 |

TABLE 19

| Ex. No. | R¹ | R² | R³ | R⁴ | Melting point °C. |
|---|---|---|---|---|---|
| 111 | —CH₃ | —CO₂CH(CH₃)₂ | 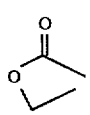 | | 226 |
| 112 | —CH₃ | —CO₂C₂H₅ | 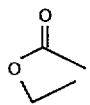 | | 218 |
| 113 | —CH₃ | —CO₂CH(CH₃)₂ | —NO₂ | —CH₃ | 229 |
| 114 | —CH₃ | —CO₂C₂H₅ | —NO₂ | —CH₃ | 234 |
| 115 | —CH₃ | —CO₂C₂H₅ | —CN | —CH₃ | 220 |
| 116 | —CH₃ | —CO₂CH(CH₃)₂ | —CN | —CH₃ | 150 |
| 117 | —CH₃ | —CN | —CN | —CH₃ | 280 |

We claim:

1. A dihydropyridine of the formula in which

R¹ and R⁴ each independently is amino or $C_1$–$C_3$-alkyl,

R³ is cyano, nitro, formyl or optionally substituted $C_1$–$C_4$-alkoxycarbonyl wherein the substituent is a $C_1$–$C_4$-alkoxy group, or R³ and R⁴ together from a radical of the formula

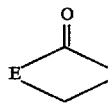

wherein E is oxygen or sulfur, $R^{25}$ is phenyl, which is optionally and independently substituted up to twice by fluorine, chlorine or methyl, $R^{13}$ is a hydrocarbon radical having up to 8 carbon atoms, which is optionally interrupted by oxygen, or a pharmaceutically acceptable salt thereof.

2. A dihydropyridine according to claim 1 which is of the formula

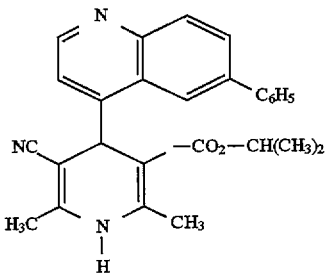

or

-continued

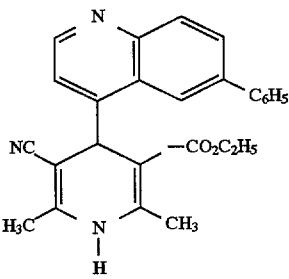

3. A calcium-agonistic composition comprising an amount effective therefor of a compound or salt thereof according to claim 1, and a pharmaceutically acceptable diluent.

4. A method of combatting a cardiovascular disease which involves cardiac insufficiency which comprises administering to a patient in need thereof of calcium agonistic effective amount of a dihydropyridine or salt thereof according to claim 1.

* * * * *

UNITED STATES PATENT AND TRADEMARK OFFICE
CERTIFICATE OF CORRECTION

PATENT NO. : 5,721,248

DATED : February 24, 1998

INVENTOR(S) : Straub, et al.

It is certified that error appears in the above-identified patent and that said Letters Patent is hereby corrected as shown below:

Title Page    FOREIGN PATENT DOCUMENTS:  Delete " 0538960 " and substitute -- 0538690 --

Signed and Sealed this

Twelfth Day of January, 1999

*Attest:*

*Attesting Officer*    Acting Commissioner of Patents and Trademarks